United States Patent
Wang et al.

(10) Patent No.: US 12,215,085 B2
(45) Date of Patent: Feb. 4, 2025

(54) CHOLINESTERASE INHIBITOR POLYMORPH AND APPLICATION THEREOF

(71) Applicants: CHANGCHUN HUAYUAN HIGH-SCIENCE AND TECHNOLOGY CO., Changchun (CN); JIANGSU SHENERYANG HIGH-SCIENCE AND TECHNOLOGY CO., Taizhou (CN)

(72) Inventors: Tonghui Wang, Changchun (CN); Ju Zhang, Changchun (CN); Lihua Wang, Changchun (CN); Depu Wang, Changchun (CN); Yaxin Zhang, Changchun (CN); Qinghua Yu, Changchun (CN); Qi Zhang, Changchun (CN); Mingze Li, Changchun (CN)

(73) Assignees: CHANGCHUN HUAYUAN HIGH-SCIENCE AND TECHNOLOGY CO., LTD., Changchun (CN); JIANGSU SHENERYANG HIGH-SCIENCE AND TECHNOLOGY CO., LTD., Taizhou (CN)

( * ) Notice: Subject to any disclaimer, the term of this patent is extended or adjusted under 35 U.S.C. 154(b) by 857 days.

(21) Appl. No.: 17/424,699

(22) PCT Filed: Jan. 21, 2020

(86) PCT No.: PCT/CN2020/073389
§ 371 (c)(1),
(2) Date: Jul. 21, 2021

(87) PCT Pub. No.: WO2020/156360
PCT Pub. Date: Aug. 6, 2020

(65) Prior Publication Data
US 2022/0227712 A1    Jul. 21, 2022

(30) Foreign Application Priority Data
Jan. 31, 2019 (CN) .......................... 201910100045.9

(51) Int. Cl.
*C07D 219/10*    (2006.01)
*A61P 25/28*    (2006.01)

(52) U.S. Cl.
CPC ............ *C07D 219/10* (2013.01); *A61P 25/28* (2018.01); *C07B 2200/13* (2013.01)

(58) Field of Classification Search
CPC .... C07D 219/10; A61P 25/28; C07B 2200/13
See application file for complete search history.

(56) References Cited

FOREIGN PATENT DOCUMENTS

| CN | 1523016 | | 8/2004 |
|---|---|---|---|
| CN | 1523016 A | * | 8/2004 |
| CN | 109651248 | | 4/2019 |
| CN | 109734663 | | 5/2019 |
| CN | 109796405 | | 5/2019 |
| CN | 110683987 | | 1/2020 |
| WO | 02079166 | | 10/2002 |

OTHER PUBLICATIONS

PCT Search Report and Written Opinion, mailed Apr. 20, 2020, received in PCT Application No. PCT/CN2020/073389. 8 pages.
Zhao, Xia et al. "A single-center, randomized, open-label, dose-escalation study to evaluate 1-9 the pharmacokinetics of tacrine analogue octahydrogenacridine succinate tablets in healthy Chinese subjects," Biological & Pharmaceutical Bulletin, vol. 35, No. 9, Dec. 31, 2021, pp. 1502-1508.
Lin Yu et al. "Study of rats with beta-amyloid injection into hippocampus to establish a memory impairment model," Chin J Psychiatry, 2000, pp. 222-225.
Zhao Xian-lin, et al. Establishment of Vascular Dementia Model in Rats, J Chin Med Univ, 2002, pp. 166-168.
S. Byrn et al, Pharmaceutical Solids: A Strategic Approach to Regulatory Considerations, Pharmaceutical research, vol. 12, No. 7, 1995, pp. 945-954.
J. K. Haleblian and W. McCrone, Pharmaceutical Applications of Polymorphism, Journal of Pharmaceutical Sciences, vol. 58, No. 8, 1969, pp. 911-929.
Cong Wei-Hong, et al. Progress in the study of animal models of Alzheimer's disease, Chinese Pharmacological Bulletin, 2003, pp. 497-501.
Shen Yu-Xian, et al., Learning and memory dysfunction in rats induced by beta-amyloid peptide fragment 25-35, Chinese Pharmacological Bulletin, 2001, 17 (1): 26-19, 4 pages.

* cited by examiner

*Primary Examiner* — Matthew P Coughlin
*Assistant Examiner* — Quincy McKoy
(74) *Attorney, Agent, or Firm* — Grossman, Tucker, Perreault & Pfleger, PLLC

(57) ABSTRACT

A cholinesterase inhibitor polymorph, wherein specifically disclosed are a octahydroaminoacridine succinate polymorph, a corresponding crystal composition and pharmaceutical composition, and applications thereof. The compound octahydroaminoacridine succinate is used for screening and studying polymorphs, and the discovered polymorphs are appraised and evaluated; crystal forms having better physical and chemical properties are determined for subsequent development and study, and crystal forms having good stability and an excellent therapeutic effect are obtained.

20 Claims, 11 Drawing Sheets

CHOLINESTERASE INHIBITOR POLYMORPH AND APPLICATION THEREOF

TECHNICAL FIELD

The present invention relates to the technical field of biological medicines, in particular to polymorphic forms of a cholinesterase inhibitor and use thereof, and specifically relates to polymorphic form of octahydroaminoacridine succinate and use thereof.

BACKGROUND INFORMATION

Drug molecules usually have a plurality of arrangements, and different arrangements form different crystal forms, i.e., the polymorphy of the drug, which generally represents the existence form of the drug raw material in a solid state. The same drug can have a plurality of crystal forms, and different crystal forms of the same drug can be dissolved and absorbed in vivo differently, so that the dissolution and release of the formulation thereof can be naturally influenced, and the clinical treatment effect and safety are further influenced.

Therefore, the crystal form of the drug is directly related to the quality and the treatment effect of the drug, the study on the polymorphic form and the property of the drug has a variety of meanings and values. Through the polymorphic form study, the crystal form stability of the drug in the preparation and storage processes can be ensured; the medicine is prepared by selecting the medicinal dominant crystal form, so that the dissolution speed and the bioavailability of the medicine can be improved, the treatment effect of the medicine can be improved, and the toxicity can be reduced; the pharmaceutical equivalency between batches in the production can be effectively ensured by determining the preparation process and improving tableting performance of drug powder according to the characteristics of crystal forms; by selecting the crystal form which has reliable, stable and controllable clinical treatment effect, an oral solid preparation with high-efficiency, low-toxicity, safety and high-quality can be prepared. Octahydroaminoacridine succinate, having a chemical name of 9-amino-1,2,3,4,5,6,7,8-octahydroacridine succinate, belongs to a new generation cholinesterase inhibitor, which simultaneously inhibits acetylcholinesterase and butyrylcholine esterase, thereby being a dual cholinesterase inhibitor. Its molecular formula is $C_{17}H_{24}N_2O_4$, and the molecular weight is 320.38. Since 2002, it was reported in literatures from dozens of countries that, compared with a high selectivity acetylcholinesterase inhibitor (donepezil), a dual cholinesterase inhibitor (rivastigmine) clinically shows better treatment effect and prospect in the treatment of senile dementia, and particularly when the donepezil treatment is ineffective for severe senile dementia patients, using rivastigmine can generate obvious treatment effect. In vitro tests show that the inhibiting ability of octahydroaminoacridine succinate to cholinesterases B and D is 500 times and 2000 times that of rivastigmine respectively. According to theoretical calculations, octahydroaminoacridine succinate will have a better clinical therapeutic effect than rivastigmine.

The primary pharmacological action of octahydroaminoacridine succinate is to selectively inhibit the activity of acetylcholinesterase in brain, correspondingly increase the content of acetylcholine between synapses in brain, and connect the main areas (hippocampal region, cerebral cortex and amygdaloid body) for memory generation and information processing with the basal brain region, and it is an effective acetylcholinesterase inhibitor, which can better penetrate blood brain barrier, concentrate acetylcholine in nerve tendon by inhibiting acetylcholinesterase and can keep longer action time, its pharmacological mechanism is to selectively block certain subtypes of potassium channels in the cell membrane and inhibit acetylcholinesterase. In addition, it can restore the excitation of peripheral nervous system, stimulate muscle nerve conduction, stimulate central nervous system, promote the contraction of smooth muscle organ, and change memory and learning ability. It has better treatment effects on preventing and treating senile dementia, preventing and treating cerebral hemorrhage and apoplexy sequelae, and preventing and treating attention deficit syndrome of teenagers, and brain strengthening and intelligence development.

Chinese patent application CN1523016A discloses the preparation of octahydroaminoacridine succinate in Example 1, but does not study its crystal form structure.

The study object of the present application is to seek new crystal forms of octahydroaminoacridine succinate, improve its bioavailability and improve its treatment effect, and hope to provide more qualitative and quantitative information for the treatment effect research of solid drugs at the same time.

SUMMARY

(I) Technical Problem to be Solved

The present invention screens and researches the polymorphic forms of the compound octahydroaminoacridine succinate, identifies and evaluates the discovered polymorphic forms, and determines the crystal forms with better physicochemical properties for subsequent research and development, aiming at providing the crystal form of octahydroaminoacridine succinate with good stability and excellent treatment effect.

(II) Technical Solutions

In order to solve the above-mentioned technical problems, the present invention provides crystal forms of octahydroaminoacridine succinate, wherein the crystal form is any of the following crystal forms:

Crystal Form A, having main characteristic diffraction peaks at the corresponding positions of 2θ values of 8.8°±0.2°, 16.4°±0.2°, 23.2°±0.2° in the X-ray powder diffraction pattern.

Crystal Form C, having main characteristic diffraction peaks at the corresponding positions of 2θ values of 8.0°±0.2°, 24.1°±0.2°, 21.7°±0.2° in the X-ray powder diffraction pattern.

Crystal Form F, having main characteristic diffraction peaks at the corresponding positions of 2θ values of 21.3°±0.2°, 7.1°±0.2°, 26.3°±0.2° in the X-ray powder diffraction pattern.

Furthermore, Crystal Form A, having secondary characteristic diffraction peaks at the corresponding positions of 2θ values of 17.0°±0.2°, 17.8°±0.2°, 23.8°±0.2° in the X-ray powder diffraction pattern;

Crystal Form C, having secondary characteristic diffraction peaks at the corresponding positions of 2θ values of 25.5°±0.2°, 22.8°±0.2°, 17.0°±0.2° in the X-ray powder diffraction pattern;

Crystal Form F, having secondary characteristic diffraction peaks at the corresponding positions of 2θ values of 24.2°±0.2°, 8.3°±0.2°, 14.2°±0.2° in the X-ray powder diffraction pattern.

Still further, Crystal Form A, having tertiary characteristic diffraction peaks at the corresponding positions of 2θ values of 12.1°±0.2°, 8.2°±0.2°, 9.3°±0.2° in the X-ray powder diffraction pattern.

Still further, Crystal Form A has an X-ray powder diffraction pattern substantially as shown in FIG. 1; Crystal Form C has an X-ray powder diffraction pattern substantially as shown in FIG. 2; Crystal Form F has an X-ray powder diffraction pattern substantially as shown in FIG. 3.

According to another aspect of the present invention, the present invention provides a process for preparing the aforementioned crystal forms of octahydroaminoacridine succinate;

Crystal Form A is prepared by any method of anti-solvent addition, anti-anti-solvent addition, gas-solid diffusion, slow volatilization, slow cooling, suspension stirring at room temperature, suspension stirring at 50° C., suspension stirring at 70° C., cyclical stirring at 50-5° C. stirring at 50-5° C., gas-liquid diffusion, high polymer induced crystallization with volatilization, high polymer induced crystallization with stirring and grinding.

Crystal Form C is prepared by any method of anti-solvent addition, anti-anti-solvent addition, slow cooling, suspension stirring at room temperature, suspension stirring at 50° C., suspension stirring at 70° C., cyclical stirring at 50-5° C. stirring at 50-5° C., gas-liquid diffusion.

Crystal Form F is prepared by gas-solid diffusion or suspension stirring at room temperature.

According to a further aspect of the present invention, the present invention provides a crystalline composition comprising any one or more of the crystal forms selected from the group consisting of the aforementioned Crystal Form A, the aforementioned Crystal Form C, and the aforementioned Crystal Form F.

Further, Crystal Form A, Crystal Form C, or Crystal Form F in the crystalline composition comprises 50% or more, preferably 80% or more, more preferably 90% or more, most preferably 95% or more by weight of the crystalline composition.

According to a further aspect of the present invention, the present invention provides a pharmaceutical composition, said pharmaceutical composition contains an effective amount of the aforementioned Crystal Form A, or the aforementioned Crystal Form C, or the aforementioned Crystal Form F, or the aforementioned crystalline composition.

Further, the pharmaceutical composition also includes carriers or excipients, commonly accepted in the art and used for the delivery of bioactive compounds to organisms (e.g., humans).

Excipients or carriers include flavoring agents, pharmaceutical grade dyes or pigments, solvents, co-solvents, buffer systems, surfactants, preservatives, sweeteners, viscosity agents, fillers, lubricants, glidants, disintegrants, binders and resins.

Conventional flavoring agents, such as those described in Remington's Pharmaceutical Sciences, 18thEd., Mack Publishing Co., 1288-1300 (1990), which is incorporated herein by reference, may be used. The pharmaceutical compositions of the present invention typically comprise from 0% to about 2% of the flavoring agent.

Conventional dyes and/or pigments, such as those described in Handbook of Pharmaceutical Excipients, by the American Pharmaceutical Association & the Pharmaceutical Society of Great Britain, 81-90 (1986), which is incorporated herein by reference, may be used. The pharmaceutical compositions of the present invention typically comprise from 0% to about 2% of the dye and/or pigment.

The pharmaceutical compositions of the present invention generally comprise from about 0.1% to about 99.9% of the solvent. The preferred solvent is water. The preferred co-solvents include ethanol, glycerol, propylene glycol, polyethylene glycol, and the like. The pharmaceutical compositions of the present invention may comprise from 0% to about 50% of the co-solvent.

The preferred buffer systems comprise acetic acid, boric acid, carbonic acid, phosphoric acid, succinic acid, malic acid, tartaric acid, citric acid, acetic acid, benzoic acid, lactic acid, glyceric acid, gluconic acid, glutaric acid and glutamic acid and sodium, potassium and ammonium salts thereof. The particularly preferred buffers are phosphoric acid, tartaric acid, citric acid and acetic acid and salts thereof. The pharmaceutical compositions of the present invention typically comprise from 0% to about 5% of the buffer.

The preferred surfactants comprise polyoxyethylene sorbitan fatty acid esters, polyoxyethylene monoalkyl ethers, sucrose monoesters and lanolin esters and ethers, alkyl sulfate salts and sodium, potassium and ammonium salts of fatty acids. The pharmaceutical compositions of the present invention typically comprise from 0% to about 2% of the surfactant.

The preferred preservatives comprise phenol, alkyl esters of para-hydroxybenzoic acid, orthophenylphenol benzoic acid and salts thereof, boric acid and salts thereof, sorbic acid and salts thereof, chlorobutanol, benzyl alcohol, thimerosal, phenylmercuric acetate and nitrate, nitromersol, benzalkonium chloride, cetylpyridinium chloride, methylparaben and propylparaben. The particularly preferred preservatives are the salts of benzoic acid, cetylpyridinium chloride, methyl paraben and propyl paraben. The pharmaceutical compositions of the present invention typically comprise from 0% to about 2% of the preservative.

The preferred sweeteners include sucrose, dextrose, saccharin, sorbitol, mannitol and aspartame. The particularly preferred sweeteners are sucrose and saccharin. The pharmaceutical compositions of the present invention typically comprise from 0% to about 5% of the sweetener.

The preferred viscosity agents include methylcellulose, sodium carboxymethylcellulose, hydroxypropyl-methylcellulose, hydroxypropylcellulose, sodium alginate, carbomer, polyvinylpyrrolidone, acacia, guar gum, xanthan gum, and tragacanth. The particularly preferred viscosity agents are methylcellulose, carbomer, xanthan gum, guar gum, polyvinylpyrrolidone, sodium carboxymethylcellulose, and magnesium aluminum silicate. The pharmaceutical compositions of the present invention typically comprise from 0% to about 5% of the viscosity agent.

The preferred fillers include lactose, mannitol, sorbitol, tribasic calcium phosphate, dibasic calcium phosphate, compressible sugar, starch, calcium sulfate, dextrorotatory (dextro) and microcrystalline cellulose. The pharmaceutical compositions of the present invention typically comprise from 0% to about 90% of the filler.

The preferred lubricants/glidants include magnesium stearate, stearic acid and talc. The pharmaceutical compositions of the present invention generally comprise from 0% to 7%, preferably from about 1% to about 5% of the lubricant/glidant.

The preferred disintegrants include starch, sodium starch glycolate, crospovidone and croscarmellose sodium and microcrystalline cellulose. The pharmaceutical compositions of the present invention generally comprise from 0% to about 20%, preferably from about 4% to about 15% of the disintegrant.

The preferred binders include acacia, tragacanth, hydroxypropylcellulose, pregelatinized starch, gelatin, polyvinylpyrrolidone, hydroxypropylcellulose, hydroxypropylmethylcellulose, methylcellulose, sugar solutions (such as sucrose and sorbitol), and ethylcellulose. The pharmaceutical compositions of the present invention generally comprise from 0% to about 12%, preferably from about 1% to about 10% of the binder.

The crystal forms, crystalline compositions, and pharmaceutical compositions described herein may be administered by any method that delivers them to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the subject. Those skilled in the art are familiar with the administration techniques that can be used for the crystal forms, crystalline compositions, and pharmaceutical compositions and methods of the present invention. By way of example only, the crystal forms, crystalline compositions, and pharmaceutical compositions described herein may be administered locally to the area in need of treatment, by for example, local infusion during surgery, topical application such as creams or ointments, injection, catheter, or implant, said implant made for example of a porous, non-porous, or gelatinous material, including membranes, such as silicone rubber membranes, or fibers. Administration can also be performed via direct injection at the site of the diseased tissue or organ.

The pharmaceutical compositions described herein may be in a form suitable for oral administration, such as, for example, lozenges, capsules, pills, powders, sustained release formulations, solutions, suspensions; in a form suitable for parenteral injection, such as sterile solutions, suspensions or emulsions; in a form suitable for topical administration, such as ointments or creams; or in a form suitable for rectal administration, such as a suppository. The pharmaceutical composition may be in unit dosage form suitable for single administration of precise dosages.

The amount of the pharmaceutical composition administered in the present invention will depend, first of all, on the mammal to be treated. In the case of administration of a pharmaceutical composition to a human subject, the daily dosage will generally be determined by the prescribing physician and will generally vary with the age, sex, diet, weight, general health and response of the individual patient, the severity of the patient's symptoms, the precise indication or disorder being treated, the severity of the indication or disorder being treated, the time of administration, the route of administration, the disposition of the composition, the rate of excretion, the pharmaceutical combination, and the judgment of the prescribing physician. In addition, the route of administration may vary depending on the disorder and its severity. The pharmaceutical composition may be in unit dosage form. In such dosage forms, the preparation is subdivided into unit doses containing appropriate quantities of the active component, e.g., an effective amount to achieve the desired purpose. It is within the skill of the relevant art to determine the appropriate dosage for a particular situation. For convenience, the total daily dosage may be administered in portions during the day, if desired. The dosage and frequency of administration will be adjusted according to the judgment of the attending physician (physician) taking into account these factors as described above. Thus, the amount of the pharmaceutical composition to be administered can vary widely. Administration can be in an amount of about 0.001 mg/kg body weight/day to about 100 mg/kg body weight/day (administered in single or divided doses), or at least about 0.1 mg/kg body weight/day.

The pharmaceutical compositions described herein may be administered as a monotherapy or in combination with another therapy or other therapies. The pharmaceutical compositions described herein and the pharmaceutical agents used in the other therapies may be administered simultaneously, sequentially or separately, depending on the nature of the disease, the condition of the patient, and the actual choice of other pharmaceutical agents to be administered. For example, a pharmaceutical composition as described herein can be administered first, followed by administration of other pharmaceutical agents; or the other pharmaceutical agent can be administered first, followed by administration of the pharmaceutical composition as described herein. This alternating administration can be repeated during a single treatment regimen. After assessing the disease being treated and the condition of the patient, a skilled clinician can determine the order of administration during the treatment regimen, and the number of repeated administrations of each drug. For example, the other pharmaceutical agents can be administrated first, and then continue the treatment with administration of the pharmaceutical composition as described herein, followed by administration of the other pharmaceutical agents, if determined to be beneficial, and so on until the treatment regimen is completed. Thus, based on experience and knowledge, a physician can vary the individual dosage regimen for a particular patient as the treatment progresses. The attending physician will consider the patient's overall welfare, and more specific signs, such as alleviation of disease-related symptoms, in determining whether treatment at the administered dose is effective. Improvements in relief of symptoms associated with disease (such as pain) and overall health status may also be used to help judge the effectiveness of treatment.

According to a further aspect of the present invention, the present invention provides the use of the aforementioned crystal form, crystalline composition or pharmaceutical composition of octahydroaminoacridine succinate in manufacture of a medicament for the treatment of diseases caused by excessive activation of cholinesterase.

According to a further aspect of the present invention, the present invention provides the use of the aforementioned crystal form, crystalline composition or pharmaceutical composition of octahydroaminoacridine succinate for the treatment of diseases caused by excessive activation of cholinesterase.

Further, said diseases caused by excessive activation of cholinesterase include Alzheimer disease, myasthenia gravis, myatrophy, poliomyelitis sequelae, childhood cerebral palsy, traumatic sensorimotor disorder, polyneuritis and radiculitis, abdominal distension, urine retention, paroxysmal supraventricular tachycardia, rescue of non-depolarizing muscular relaxant poisoning, glaucoma, muscle relaxant antagonism, inflammation, kidney disease, obesity, fatty liver, hyperthyroidism, schizophrenia, hemolytic anemia, and megaloblastic anemia.

According to a further aspect of the present invention, the present invention provides the use of the aforementioned crystal form, crystalline composition or pharmaceutical composition of octahydroaminoacridine succinate in manufacture of a medicament for the treatment of diseases related to decreased choline function.

According to a further aspect of the present invention, the present invention provides the use of the aforementioned crystal form, crystalline composition or pharmaceutical composition of octahydroaminoacridine succinate for the treatment of diseases related to decreased choline function.

Further, the diseases related to decreased choline function include insomnia, vascular dementia, memory loss, attention deficit disorder and other sleep disorders, and choline depletion-related cognitive impairment disease.

As used herein, the term "polymorphic form" refers to different crystal forms of the same compound and other solid state molecular forms including pseudo-polymorphs, such as hydrates (e.g., bound water present in the crystalline structure) and solvates (e.g., bound solvents other than water) of the same compound. Different crystalline polymorphic forms have different crystal structures due to a different packing of the molecules in the lattice. This results in a different crystal symmetry and/or unit cell parameters which directly influences its physical properties such the X-ray diffraction characteristics of crystals or powders. A different polymorphic form, for example, will in general diffract at a different set of angles and will give different values for the intensities. Therefore, X-ray powder diffraction can be used to identify different polymorphic forms, or a solid form that comprises more than one polymorphic form, in a reproducible and reliable way (S. Byrn et al, Pharmaceutical Solids: A Strategic Approach to Regulatory Considerations, Pharmaceutical research, Vol. 12, No. 7, p. 945-954, 1995; J. K. Haleblian and W. McCrone, Pharmaceutical Applications of Polymorphism, Journal of Pharmaceutical Sciences, Vol. 58, No. 8, p. 911-929, 1969). Crystalline polymorphic forms are of interest to the pharmaceutical industry and especially to those polymorphic forms involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphic forms may display other advantageous physical properties such as lack of hygroscopic tendencies, improved solubility, and enhanced rates of dissolution due to different lattice energies.

The term "pharmaceutical composition" refers to a mixture of one or more of the crystal forms or crystalline compositions described herein, with other chemical components, such as physiologically/pharmaceutically acceptable carriers or excipients. The purpose of a pharmaceutical composition is to facilitate administration of a compound to an organism.

An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The term "2θ value" or "2θ" refers to the peak position based on the experimental setup of the X-ray diffraction experiment and is a common abscissa unit in diffraction patterns. The experimental setup requires that if a reflection is diffracted when the incoming beam forms an angle of theta (θ) with a certain lattice plane, the reflected beam is recorded at an angle of 2 theta (2θ).

The term "X-ray powder diffraction pattern" refers to the experimentally observed diffractogram or parameters derived therefrom. X-Ray powder diffraction patterns are characterized by peak position (abscissa) and peak intensities (ordinate).

(III) Advantageous Effects

The aforementioned technical solutions of the present invention have the following advantages: good physical and chemical stabilities, high solubility and excellent treatment effect.

DETAILED DESCRIPTION

Figure 1:
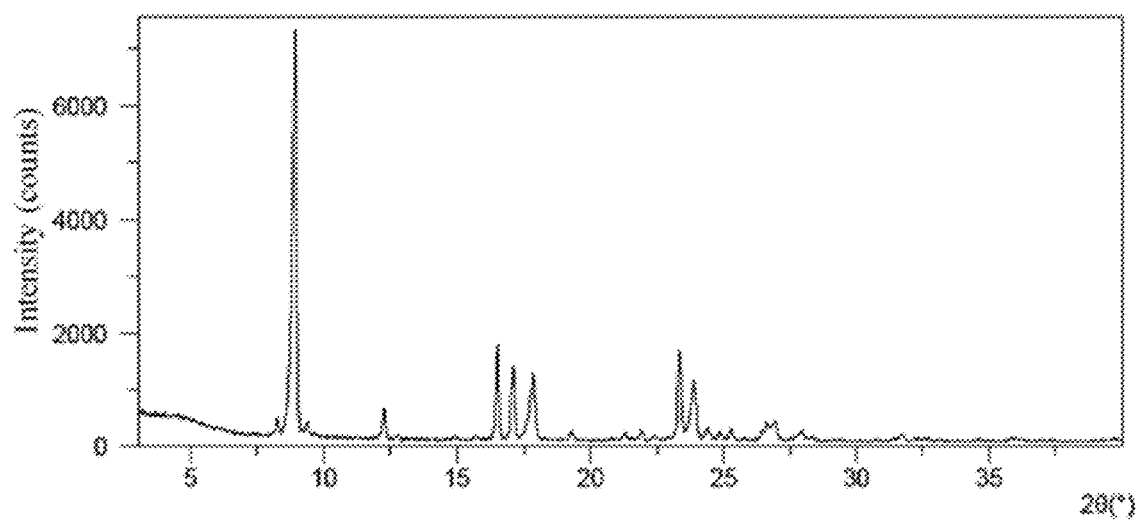
FIG. 1 shows an X-ray powder diffraction pattern of Crystal Form A.

In order to make the objects, technical solutions and advantages of the embodiments of the present invention clearer, the technical solutions in the embodiments of the present invention will be clearly and completely described below with reference to the drawings in the embodiments of the present invention, and it is obvious that the described embodiments are some, but not all, embodiments of the present invention. All other embodiments, which can be obtained by a person skilled in the art without making any inventive effort based on the embodiments in the present invention, belong to the protection scope of the present invention.

Example 1: Preparation of Polymorphic Forms of Octahydroaminoacridine Succinate 1. Preparation of Crystal Form A
1) Anti-Solvent Addition Test About 20 mg of octahydroaminoacridine succinate (trade name: Shen Er Yang, supplied by Changchun Huayang High Technology Co., Ltd) was weighed into a 20 mL vial, and dissolved in 0.2-2.0 mL of a good solvent (see Table 1). Then an anti-solvent (see Table 1) was added dropwise to the clear solution with stirring (about 1000 rpm) for 3 days to precipitate a solid, which was separated by centrifugation. * in the table: no solid was precipitated after 10 ml of the anti-solvent was added dropwise, and the system was transferred to 5° C. to be continuously stirred to precipitate a solid.

TABLE 1

Anti-solvent addition test

| Good solvent | Anti-solvent | Crystal Form |
| --- | --- | --- |
| Methanol | Acetone, ethyl acetate, methyl tert-butyl ether, toluene, 2-butanone | Crystal Form A |
| N,N-dimethyl acetamide | Methyl isobutyl ketone | Crystal Form A |
| Water | 1,4-dioxane | Crystal Form A* |

2) Anti-Anti-Solvent Addition

About 20 mg of octahydroaminoacridine succinate was weighed into a 20 mL vial, and dissolved in 0.4-2.0 mL of a good solvent (see Table 2). Then the resulting solution was added dropwise to a 20 mL vial containing 8 mL of an anti-solvent (see Table 2) with stirring (about 1000 rpm). If a solid was precipitated, the precipitated solid was separated out by centrifugation and tested by XRPD. * in the table: no solid was precipitated, and the system was transferred to 5° C. to be continuously stirred to precipitate a solid; #in the table: no solid was precipitated, the system was transferred to 5° C. to be continuously stirred, but was still clear, and the system was transferred to room temperature and volatilized to precipitate a solid.
2) Anti-Anti-Solvent Addition Test

| Good solvent | Anti-solvent | Crystal Form |
| --- | --- | --- |
| Methanol | Methyl isobutyl ketone | Crystal Form A |
|  | Methylene chloride | Crystal Form A# |
|  | Isobutyl acetate | Crystal Form A |
|  | n-Octanol | Crystal Form A* |

3) Gas-Solid Diffusion

About 15 mg of octahydroaminoacridine succinate was weighed into each of 3 mL vials, and to each of 20 mL vials was added about 4 mL of a solvent (methylene chloride, methanol, acetonitrile, tetrahydrofuran, acetone, dimethyl sulfoxide, ethyl acetate, 1,4-dioxane, isopropanol, water (22.5% relative humidity), water (43.2% relative humidity), water (57.6% relative humidity), or water (75.3% relative humidity)), the 3 mL vial being open was placed in the 20 mL vial, and the 20 mL vial was sealed. After the system was stood at room temperature for 9 days, the solid was collected.

4) Slow Volatilization

About 15 mg of octahydroaminoacridine succinate was weighed into each of 3 ml vials, and 0.4-3.0 mL of methanol, isopropanol, or water/tetrahydrofuran (1:1) was added respectively. The system was filtered under shaking to obtain its supernatant. The vial containing a clear solution was sealed with a sealing film, and several pinholes were pricked into the sealing film. The vial was placed at room temperature for slow volatilization. When the solvent was completely volatilized, the resulting solid was collected.

5) Slow Cooling

About 20 mg of octahydroaminoacridine succinate was weighed into each of 5 mL vials, and 1.0-3.0 mL isopropanol, or methanol/isopropyl acetate (1:4) was added respectively. The system was stirred at 50° C. for 2 hours and then filtered to obtain a supernatant. The obtained supernatant was placed in a biochemical incubator, and cooled from 50° C. to −20° C. at a cooling rate of 0.1° C./minute and the precipitated solid was then collected.

6) Suspension Stirring at Room Temperature

About 20 mg of octahydroaminoacridine succinate was weighed into each of HPLC vials, and 0.3 mL of isopropanol, acetone, isopropyl acetate, methyl tert-butyl ether, 2-methyltetrahydrofuran, acetonitrile, methylene chloride, n-heptane, cumene, 2-butanone, methanol/methyl isobutyl ketone (1:9), absolute ethyl alcohol/ethyl acetate (1:4), tetrahydrofuran/anisole (1:1), trichloromethane/n-heptane (1:9), dimethyl sulfoxide/cyclohexane (1:9), methyl tert-butyl ether/2-butanone (1:9), acetonitrile/acetone (1:1), methanol/toluene (1:9), isopropanol/2-methyltetrahydrofuran (1:1), acetone/1,4-dioxane (1:1), trichloromethane/m-xylene (1:1), n-octanol/1,4-dioxane (1:1), acetonitrile/water (aw~0.2, 99:1), acetonitrile/water (aw~0.4, 98:2), acetonitrile/water (aw~0.6, 96:4), or acetonitrile/water (aw~0.8, 92:8) was added respectively, and the resulting turbid solution was stirred with magnetic stirrer (about 1000 rpm) at room temperature for about 3 days, and then the solid was collected by centrifugation.

7) Suspension Stirring at 50° C.

About 25 mg of octahydroaminoacridine succinate was weighed into each of HPLC vials, and 0.4 mL of isopropanol, methyl isobutyl ketone, 1,4-dioxane, trichloromethane, toluene, n-octanol, anisole, m-xylene, absolute ethyl alcohol/acetonitrile (1:4), acetone/1,4-dioxane (1:1), 2-butanone/n-heptane (1:1), toluene/m-xylene (1:1), isopropanol/cumene (1:1), water/acetone (1:9), isobutyl acetate/n-heptane (1:1), 1,4-dioxane/anisole (1:1), or n-octanol/isopropyl acetate (1:1) was added respectively, and the resulting turbid solution was stirred with magnetic stirrer (about 1000 rpm) at 50° C. for about 3 days, and then the solid was collected by centrifugation. 8) Suspension stirring at 70° C.

About 25 mg of octahydroaminoacridine succinate was weighed into each of HPLC vials, and 0.5 mL of isopropanol, 2-methyltetrahydrofuran, 1,4-dioxane, toluene, cyclohexane, 1,4-dioxane/ethyl acetate (1:1), methyl isobutyl ketone/n-heptane (1:1), acetonitrile/n-octanol (1:1), cumene/toluene (1:1), anisole/isopropyl acetate (1:1), cyclohexane/acetonitrile (1:1), m-xylene/2-methyltetrahydrofuran (1:1), or n-heptane/isopropanol (1:1) was added respectively, and the resulting turbid solution was stirred with magnetic stirrer (about 1000 rpm) at 70° C. for about 3 days, and then the solid was collected by centrifugation.

9) Cyclical Stirring at 50-5° C.

About 20 mg of octahydroaminoacridine succinate was weighed into each of HPLC vials, and 0.4 mL of isopropanol, acetone, methyl tert-butyl ether, acetonitrile, n-heptane, cumene, methyl isobutyl ketone (1:1), toluene/anisole (1:1), n-heptane/acetonitrile (1:1), or N,N-dimethyl acetamide/methyl tert-butyl ether (1:9) was added respectively, and the resulting suspension was stirred with magnetic stirrer at 50° C. for 2 hours, then cooled to 5° C. at a cooling rate of 0.1° C./min, balanced at 5° C. for 1 hour, then heated to 50° C. at the same rate. The above procedure was repeated for 3 cycles. Then the system was stirred at 5° C., and the test was carried out for about 3 days. The solid was collected by centrifugation.

10) Gas-Liquid Diffusion

About each 20 mg of octahydroaminoacridine succinate was weighed into 0.43-2.0 mL of a good solvent respectively (see Table 3), the system was filtered to obtain a supernatant, and the obtained supernatant was transferred to a 3 mL vial. About 4 mL of an anti-solvent (see Table 3) was added to another 20 mL vial, and after the 3 mL vial with the supernatant being open was placed in the 20 mL vial, the 20 mL vial was sealed and allowed to stand at room temperature. When the solid was observed to precipitate, the solid was separated, and if no solid was precipitated after 16 days, the 3 mL vial was taken out and left to volatilize at room temperature, and the resulting solid was collected.

TABLE 3

Gas-liquid diffusion test

| Good solvent | Anti-solvent |
|---|---|
| absolute ethyl alcohol | Ethyl acetate |
| | Cyclohexane |
| Water | Acetone |
| | Tetrahydrofuran |
| | Acetonitrile |

11) High Polymer Induced Crystallization with Volatilization

About each 20 mg of octahydroaminoacridine succinate was weighed and dissolved into 0.4-3.0 mL of the solvent listed in Table 4 respectively. The system was filtered to obtain a supernatant, and the obtained supernatant was transferred to a 3 mL vial containing about 1 mg of mixed polymers. The vial containing the clear solution was sealed with a sealing film, and several pinholes were pricked into the sealing film. The system was placed at room temperature for slow volatilization. When the solvent was completely evaporated, the resulting solid was collected. The mixed high polymer A: polyvinyl pyrrolidone, polyvinyl alcohol, polyvinyl chloride, polyvinyl acetonitrile, hydroxypropyl methylcellulose and methylcellulose (mixed by equal mass); the mixed high polymer B: polycaprolactone, polyethylene glycol, polymethyl methacrylate, sodium alginate and hydroxyethyl cellulose (mixed by equal mass).

TABLE 4

High polymer induced (volatilization)

| Solvent | High polymer |
|---|---|
| Absolute ethyl alcohol | Mixed high polymer A |
| Methanol/butanone (1:2) | Mixed high polymer B |

12) High Polymer Induced Crystallization with Stirring

About 20 mg of octahydroaminoacridine succinate was weighed into each of HPLC vials, and each 0.3 mL of the solvent listed in Table 5 was added respectively, and the mixture was stirred with magnetic stirrer (about 1000 rpm) at room temperature for about 3 days and the resulting solid was then collected. The mixed high polymer A: polyvinyl pyrrolidone, polyvinyl alcohol, polyvinyl chloride, polyvinyl acetonitrile, hydroxypropyl methylcellulose and methylcellulose (mixed by equal mass); the mixed high polymer B: polycaprolactone, polyethylene glycol, polymethyl methacrylate, sodium alginate and hydroxyethyl cellulose (mixed by equal mass).

TABLE 5

High polymer induced (stirring)

| Solvent | High polymer |
|---|---|
| Methyl isobutyl ketone/methylene chloride (1:1) isopropyl acetate/m-xylene (1:1) | Mixed high polymer A |
| 2-Methyltetrahydrofuran/cyclohexane (1:1) acetonitrile/anisole (1:1) | Mixed high polymer B |

13) Grinding

About each 20 mg of octahydroaminoacridine succinate was weighed and put into a mortar. No solvent was added, or absolute ethyl alcohol, toluene, or ethyl formate was added dropwise respectively. The mixture was ground for 5 minutes, and a solid was collected.

2. Preparation of Crystal Form C

1) Anti-Solvent Addition Test

About 20 mg of octahydroaminoacridine succinate was weighed into a 20 mL vial, and dissolved in 0.2-2.0 mL of a good solvent (see Table 6). Then an anti-solvent (see Table 6) was added dropwise to the clear solution with stirring (about 1000 rpm) for 3 days to precipitate a solid, which was separated by centrifugation. * in the table: no solid was precipitated after 10 ml of the anti-solvent was added dropwise, and the system was transferred to 5° C. to be continuously stirred to precipitate a solid.

TABLE 6

Anti-solvent addition test

| Good solvent | Anti-solvent | Crystal form |
|---|---|---|
| N,N-dimethyl acetamide | Isobutyl acetate | Crystal form C |
| Water | Acetonitrile | Crystal form C* |

2) Anti-Anti-Solvent Addition

About 20 mg of octahydroaminoacridine succinate was weighed into a 20 mL vial, and dissolved in 0.4-2.0 mL of a good solvent (see Table 7). Then the resulting solution was added dropwise to a 20 mL vial containing 8 mL of an anti-solvent (see Table 7) with stirring (about 1000 rpm). If a solid was precipitated, the precipitated solid was separated out by centrifugation and tested by XRPD. * in the table: no solid was precipitated, and the system was transferred to 5° C. to be continuously stirred to precipitate a solid.

TABLE 7

Anti-anti-solvent addition test

| Good solvent | Anti-solvent | Crystal form |
|---|---|---|
| Absolute ethyl alcohol | Acetonitrile | Crystal form C |
| N,N-dimethyl acetamide | Ethyl acetate | Crystal form C* |
| | 1,4-Dioxane | Crystal form C* |

3) Slow Cooling

About 20 mg of octahydroaminoacridine succinate was weighed into each of 5 mL vials, and 1.0-3.0 mL absolute ethyl alcohol or absolute ethyl alcohol/acetonitrile (1:1) was added respectively. The system was stirred at 50° C. for 2 hours and then filtered to obtain a supernatant. The obtained supernatant was placed in a biochemical incubator, and cooled from 50° C. to −20° C. at a cooling rate of 0.1° C./minute and the precipitated solid was then collected.

4) Suspension Stirring at Room Temperature

About each 20 mg of octahydroaminoacridine succinate was weighed into HPLC vials, and 0.3 mL of absolute ethyl alcohol/ethyl acetate (1:4) was added, and the obtained suspension was stirred with magnetic stirrer (about 1000 rpm) at room temperature for about 3 days, and then a solid was collected by centrifugation.

5) Suspension Stirring at 50° C.

About 25 mg of octahydroaminoacridine succinate was weighed into each of HPLC vials, and 0.4 mL of ethyl acetate, 1,4-dioxane, acetylacetone, absolute ethyl alcohol/acetonitrile (1:4), acetone/1,4-dioxane (1:1), methyl isobutyl ketone/ethyl acetate (1:1), or acetylacetone/n-heptane (1:1) was added respectively, and the obtained turbid solution was stirred with magnetic stirrer (about 1000 rpm) at 50° C. for about 3 days, and then a solid was collected by centrifugation.

6) Suspension Stirring at 70° C.

About 25 mg of octahydroaminoacridine succinate was weighed into each of HPLC vials, and 0.5 mL of acetylacetone or ethyl acetate was added, and the obtained turbid solution was stirred with magnetic stirrer (about 1000 rpm) at 70° C. for about 3 days, and then a solid was collected by centrifugation.

7) Cyclical Stirring at 50-5° C.

About 20 mg of octahydroaminoacridine succinate was weighed into each of HPLC vials, and 0.4 mL of ethyl formate, acetone, ethyl acetate/cumene (1:1), acetylacetone/isopropyl acetate (1:1) was added respectively, and the resulting suspension was stirred with magnetic stirrer at 50° C. for 2 hours, then cooled to 5° C. at a cooling rate of 0.1° C./min, balanced at 5° C. for 1 hour, then heated to 50° C. at the same rate. The above procedure was repeated for 3 cycles. Then the system was stirred at 5° C., and the test was carried out for about 3 days. The solid was collected by centrifugation.

8) Gas-Liquid Diffusion

About each 20 mg of octahydroaminoacridine succinate was weighed into 0.43-2.0 mL of a good solvent (see Table 8), the system was filtered to obtain a supernatant, and the obtained supernatant was transferred to a 3 mL vial. About 4 mL of an anti-solvent (see Table 8) was added to another 20 mL vial, and after the 3 mL vial with the supernatant being open was placed in the 20 mL vial, the 20 mL vial was sealed and allowed to stand at room temperature. When the solid was observed to precipitate, the solid was separated, and if no solid was precipitated after 16 days, the 3 mL vial was taken out and left to volatilize at room temperature, and the resulting solid was collected.

TABLE 8

| Gas-liquid diffusion test | |
|---|---|
| Good solvent | Anti-solvent |
| Methanol | Acetonitrile |
| | Cyclohexane |
| Absolute ethyl alcohol | Ethyl acetate |

3. Preparation of Crystal Form F

1) Gas-Solid Diffusion

About 15 mg of octahydroaminoacridine succinate was weighed into each of 3 mL vials. About 4 mL of trichloromethane was added to another 20 mL vial, and after the 3 mL vial being open was placed in the 20 mL vial, the 20 mL vial was sealed. After the system was stood at room temperature for 9 days, the solid was collected.

2) Suspension Stirring at Room Temperature

About 20 mg of octahydroaminoacridine succinate was weighed into each of HPLC vials, and 0.3 mL of trichloromethane/n-heptane (1:9) was added, and the obtained suspension was stirred with magnetic stirrer (about 1000 rpm) at room temperature for about 3 days, and then a solid was collected by centrifugation.

4. Preparation of Crystal Form as Comparative Example

The preparation was carried out according to the method described in Example 1 of Chinese patent application CN1523016A, by dissolving 1.01 g (0.005 mol) of acridine based substance in methanol and adding 0.65 g (0.0055 mol) of succinic acid in methanol to the resulting solution. After mixing uniformly, a small amount of diethyl ether was added to the resulting mixture, and the resulting white precipitate was placed at 4° C. for 20 minutes. After filtering, the precipitate was collected and washed three times with diethyl ether and dried at 100° C. to give a solid compound.

Example 2 Characterization and Identification of Polymorphic Forms of Octahydroaminoacridine Succinate 1. X-Ray Powder Diffraction (XRPD) Detection Step: XRPD patterns were collected on a PANalytacal Empyrean X-ray powder diffraction analyzer with the scan parameters shown in Table 9.

TABLE 9

| XRPD test parameters | | |
|---|---|---|
| Parameters | Empyrean | X' Pert3 |
| X-ray | Cu, kα, Kα1 (Å): 1.540598; Kα2 (Å): 1.544426 Kα2/Kα1 intensity ratio: 0.50 | Cu, kα, Kα1 (Å): 1.540598; Kα2 (Å): 1.544426 Kα2/Kα1 intensity ratio: 0.50 |
| X-ray tube setting | 4 kV, 40 mA | 4 kV, 40 mA |
| Divergence slit | Auto | Auto |
| Monochromator | No | No |
| Scanning mode | Continuous | Continuous |
| Scanning range (°2Theta) | 3°-40° | 3°-40° |

TABLE 9-continued

XRPD test parameters

| Parameters | Empyrean | X' Pert3 |
|---|---|---|
| Scanning step (°2Theta) | 0.0167 | 0.0263 |
| Scanning time (minutes) | about 5 min 30 s | about 5 min |

Result (1) The X-ray powder diffraction results of Crystal Form A are shown in FIG. 1 and Table 10 respectively, and the allowable error of the 2θ value in Table 10 is in the range of ±0.2°.

Crystal Form A had main characteristic diffraction peaks at the corresponding positions of 2θ values of 8.8°±0.2°, 16.4°±0.2°, 23.2°±0.2°; secondary characteristic diffraction peaks at the corresponding positions of 2θ values of 17.0°±0.2°, 17.8°±0.2°, 23.8°±0.2°; tertiary characteristic diffraction peaks at the corresponding positions of 2θ values of 12.1°±0.2°, 8.2°±0.2°, 9.3°±0.2° in the X-ray powder diffraction pattern.

TABLE 10

XRPD diffraction peak data of Crystal Form A

| 2theta (°) | d spacing (Å) | intensity (%) |
|---|---|---|
| 8.16 | 10.71 | 3.74 |
| 8.81 | 9.93 | 100 |
| 9.26 | 9.45 | 3.55 |
| 12.15 | 7.23 | 7.55 |
| 12.63 | 6.95 | 0.81 |
| 14.81 | 5.94 | 0.77 |
| 15.59 | 5.65 | 0.75 |
| 16.41 | 5.37 | 23.92 |
| 17.01 | 5.18 | 18.08 |
| 17.77 | 4.97 | 16.5 |
| 19.22 | 4.59 | 2.09 |
| 21.19 | 4.17 | 1.99 |
| 21.83 | 4.05 | 2.4 |
| 22.30 | 3.97 | 1.17 |
| 23.25 | 3.81 | 22.73 |
| 23.78 | 3.73 | 15.4 |
| 24.29 | 3.65 | 3.27 |
| 24.76 | 3.58 | 2.21 |
| 25.18 | 3.52 | 2.76 |
| 26.52 | 3.35 | 4.79 |
| 26.85 | 3.31 | 4.98 |
| 27.86 | 3.19 | 2.33 |
| 31.66 | 2.82 | 1.7 |
| 32.55 | 2.74 | 0.88 |
| 35.77 | 2.50 | 0.78 |

Figure 2:
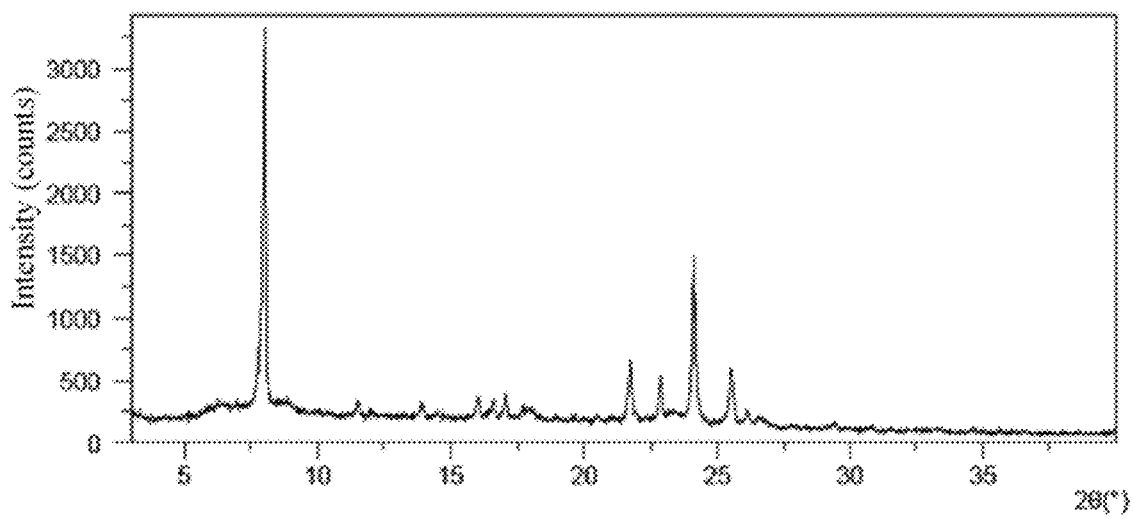
FIG. 2 shows an X-ray powder diffraction pattern of Crystal Form C.

(2) The X-ray powder diffraction results of Crystal Form C are shown in FIG. 2 and Table 11 respectively, and the allowable error of the 2θ value in Table 11 is in the range of ±0.2°.

Crystal Form C had main characteristic diffraction peaks at the corresponding positions of 2θ values of 8.0°±0.2°, 24.1°±0.2°, 21.7°±0.2°; secondary characteristic diffraction peaks at the corresponding positions of 2θ values of 25.5°±0.2°, 22.8°±0.2°, 17.0°±0.2° in the X-ray powder diffraction pattern.

TABLE 11

X-ray diffraction peak data of Crystal Form C

| 2theta (°) | d spacing (Å) | intensity (%) |
|---|---|---|
| 6.33 | 13.86 | 2.69 |
| 7.95 | 11.05 | 100 |
| 11.46 | 7.69 | 3.51 |
| 13.87 | 6.36 | 3.22 |
| 15.98 | 5.53 | 5.29 |
| 16.54 | 5.34 | 4.46 |
| 17.02 | 5.19 | 6.51 |
| 17.83 | 4.96 | 2.59 |
| 21.67 | 4.09 | 15.73 |
| 22.82 | 3.89 | 11.89 |
| 24.06 | 3.69 | 41.96 |
| 25.47 | 3.49 | 14.69 |
| 26.08 | 3.41 | 3.96 |
| 26.55 | 3.35 | 2.4 |
| 29.24 | 3.05 | 0.82 |
| 30.72 | 2.91 | 0.97 |

Figure 3:
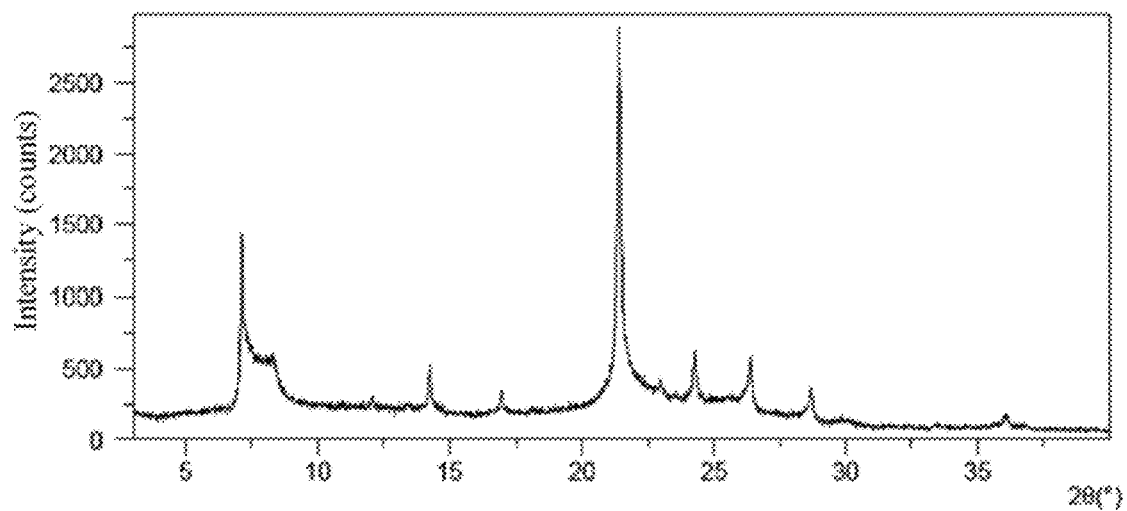
FIG. 3 shows an X-ray powder diffraction pattern of Crystal Form F.

(3) The X-ray powder diffraction results of Crystal Form F are shown in FIG. 3 and Table 12 respectively, and the allowable error of the 2θ value in Table 12 is in the range of ±0.2°.

Crystal Form F had main characteristic diffraction peaks at the corresponding positions of 2θ values of 21.3°±0.2°, 7.1°±0.2°, 26.3°±0.2°; secondary characteristic diffraction peaks at the corresponding positions of 2θ values of 24.2°±0.2°, 8.3°±0.2°, 14.2°±0.2° in the X-ray powder diffraction pattern.

TABLE 12

X-ray diffraction peak data of Crystal Form F

| 2theta (°) | d spacing (Å) | intensity (%) |
|---|---|---|
| 7.06 | 12.42 | 46.06 |
| 8.25 | 10.64 | 12.69 |
| 14.17 | 6.23 | 11.37 |
| 16.90 | 5.23 | 5.68 |
| 21.34 | 4.15 | 100 |
| 24.23 | 3.66 | 15.64 |
| 26.32 | 3.38 | 15.95 |
| 28.60 | 3.11 | 9.08 |
| 29.88 | 2.98 | 1.09 |
| 35.99 | 2.49 | 3.27 |

Figure 20:
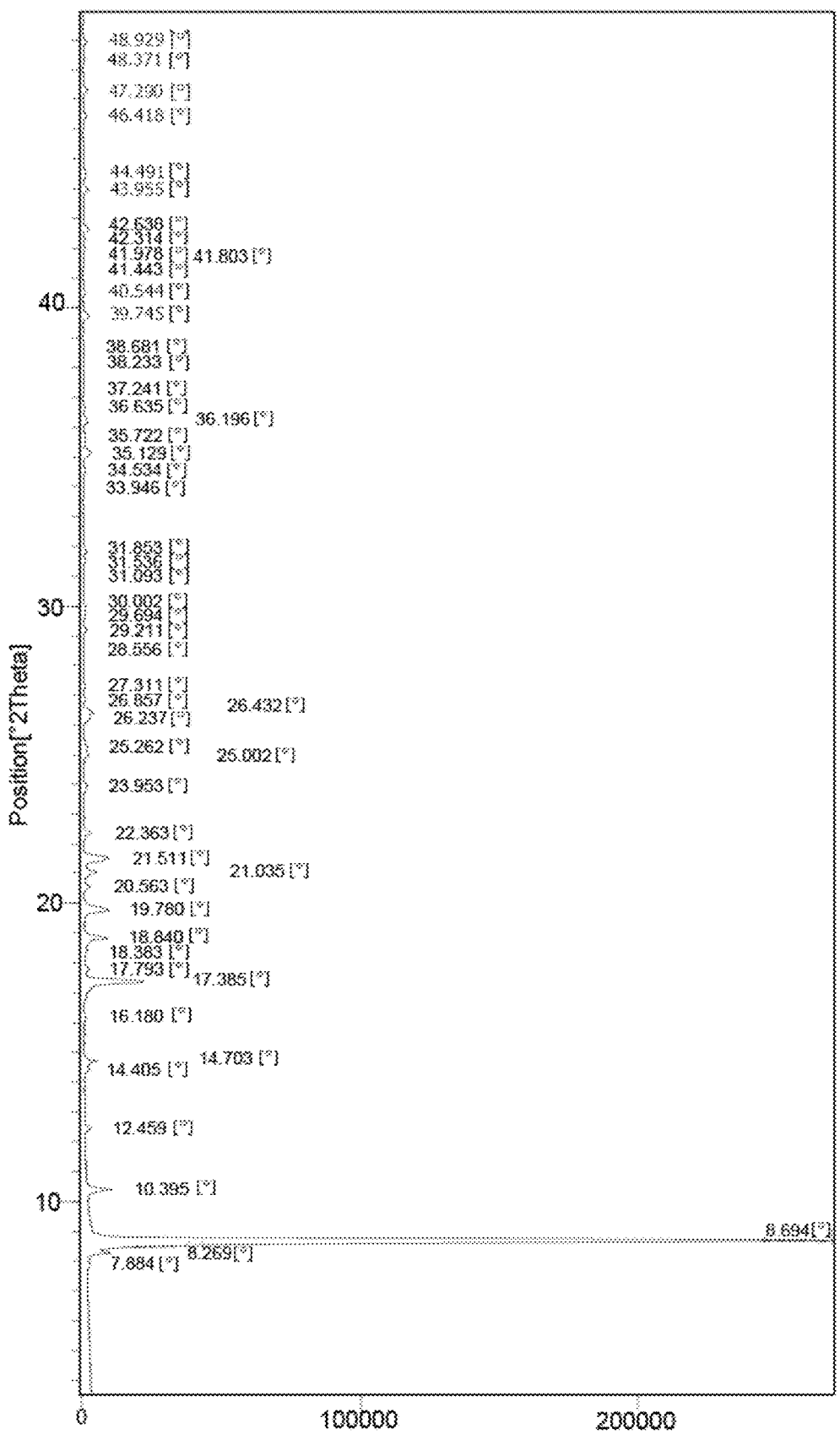
FIG. 20 shows an X-ray powder diffraction pattern of Crystal Form K as comparative example.

(4) The X-ray powder diffraction results of the crystal form of comparative example are shown in FIG. 20 and Table 13 respectively, and the allowable error of the 2θ value in Table 13 is in the range of ±0.2°. The crystal form of comparative example was named as Crystal Form K.

Crystal Form K of comparative example had main characteristic diffraction peak(s) at the corresponding position(s) of 2θ value(s) of 8.69°±0.2°; and secondary characteristic diffraction peaks at the corresponding positions of 2θ values of 17.39°±0.2°, 10.39°±0.2°, 21.51°±0.2° in the X-ray powder diffraction pattern.

TABLE 13

| X-ray diffraction peak data of Crystal Form K | | |
| --- | --- | --- |
| 2theta (°) | d spacing (Å) | intensity (%) |
| 8.2690 | 10.69290 | 3.12 |
| 8.6937 | 10.17151 | 100.00 |
| 10.3951 | 8.51017 | 3.45 |
| 12.4595 | 7.10442 | 0.74 |
| 14.7026 | 6.02519 | 1.66 |
| 17.3853 | 5.10101 | 7.85 |
| 18.8402 | 4.71026 | 3.08 |
| 19.7797 | 4.48859 | 3.08 |
| 20.5629 | 4.31937 | 0.84 |
| 21.0348 | 4.22351 | 1.67 |
| 21.5113 | 4.13104 | 3.36 |
| 22.3627 | 3.97564 | 0.85 |
| 26.2375 | 3.39665 | 0.84 |
| 26.4320 | 3.37209 | 1.40 |
| 35.1289 | 2.55465 | 0.89 |
| 39.7452 | 2.26793 | 0.71 |
| 43.9545 | 2.06001 | 0.71 |

2. Thermogravimetric Analysis (TGA) and Differential Scanning Calorimetry (DSC) Detection Step: TGA was collected on a TA Q500/5000 thermogravimetric analyzer, DSC was collected on a TA Q200/2000 differential scanning calorimeter, and the collection parameters are shown in Table 14.

TABLE 14

| TGA and DSC test parameters | | |
| --- | --- | --- |
| Parameters | TGA | DSC |
| Method | Linear heating | Linear heating |
| Sample pan | Aluminum pan, open | Aluminum pan, closed with a lid |
| Temperature range | Room temperature to a set final temperature | 25° C. to a set final temperature |
| Scan rate (° C./minutes) | 10 | 10 |
| Protection gas | Nitrogen | Nitrogen |

Result

Figure 4:
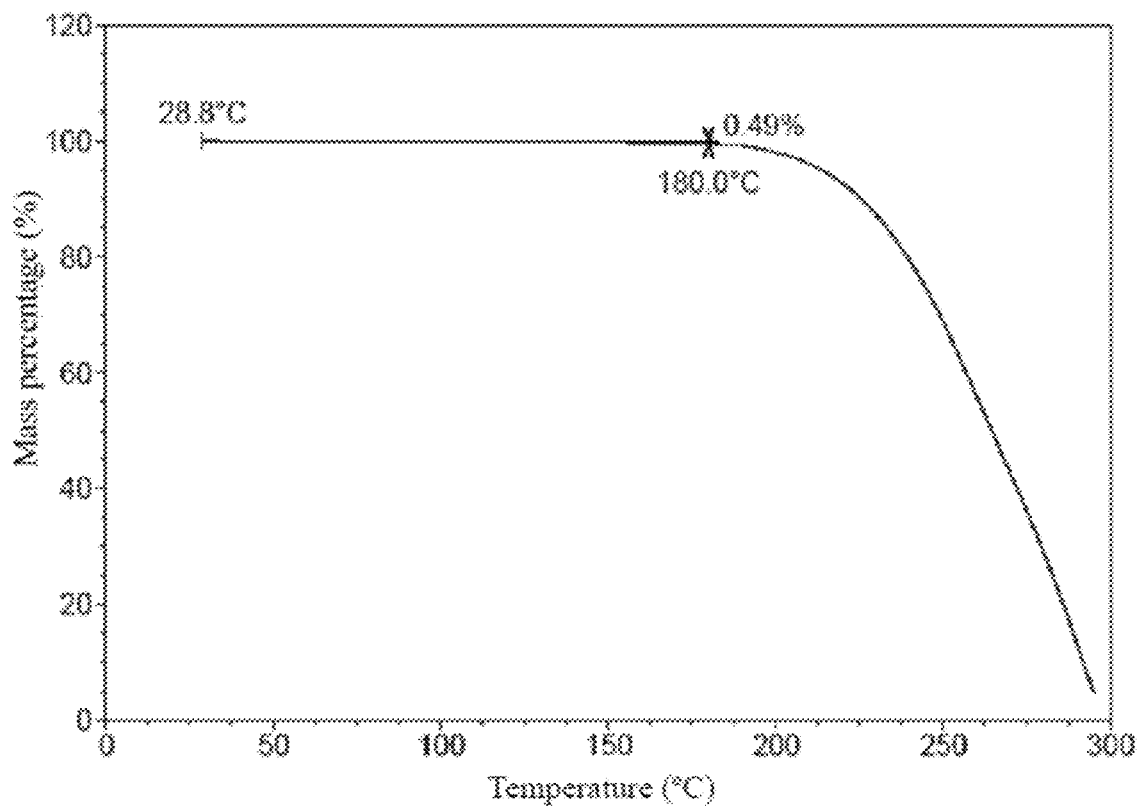
FIG. 4 shows a TGA profile of Crystal Form A.
Figure 5:
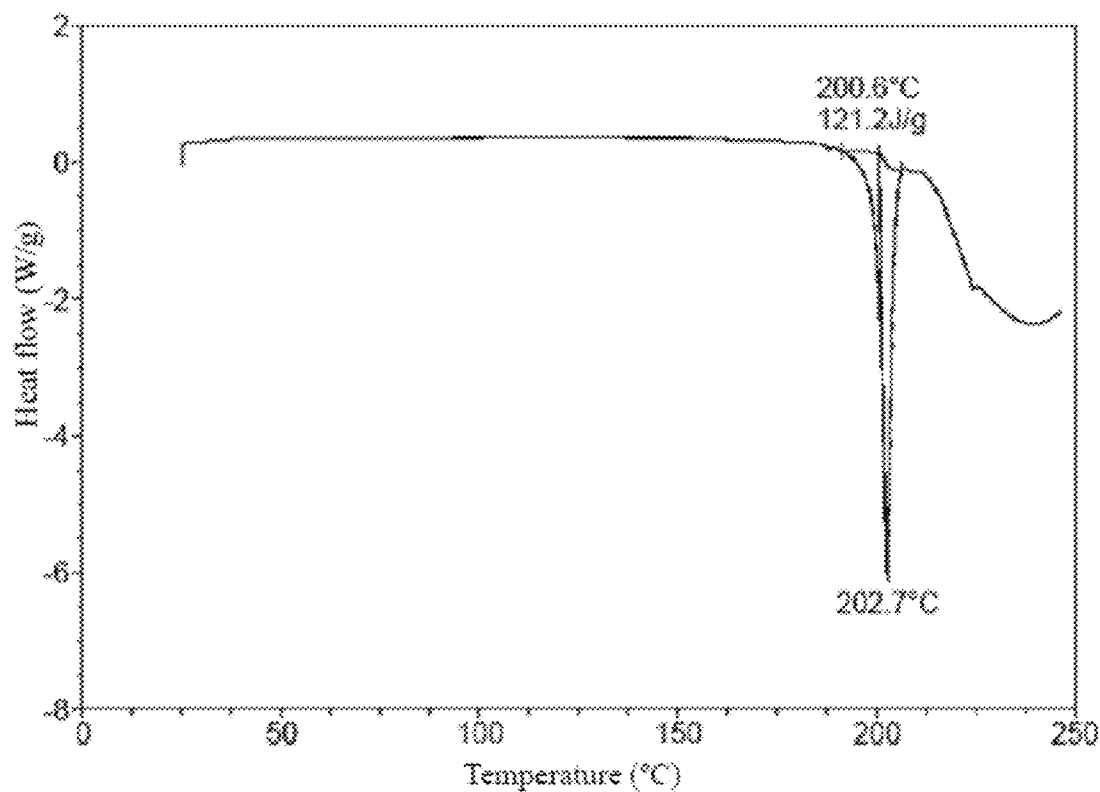
FIG. 5 shows a DSC profile of Crystal Form A.

The thermogravimetric analysis result of Crystal Form A is shown in FIG. 4, and the differential scanning calorimetry result is shown in FIG. 5. Crystal Form A had a sharp melting endothermic peak at 200.6° C. (initial temperature), and the weight loss of Crystal Form A was 0.5% when Crystal Form A was heated to 180° C.

Figure 6:
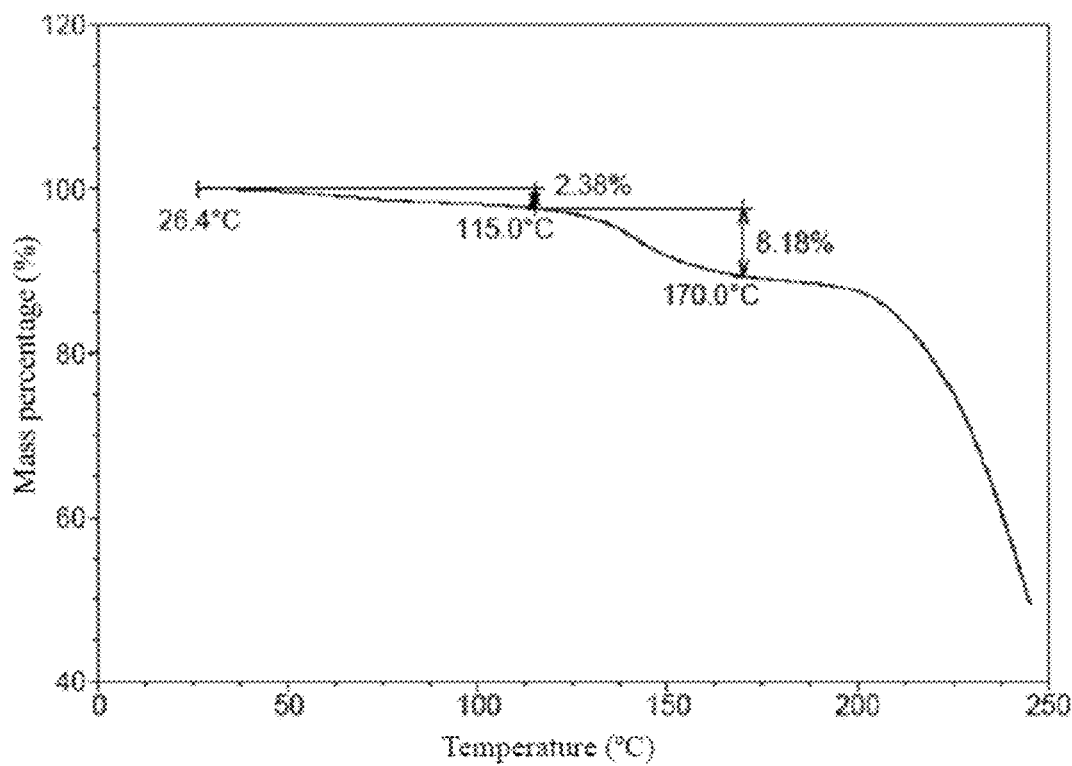
FIG. 6 shows a TGA profile of Crystal Form C.
Figure 7:
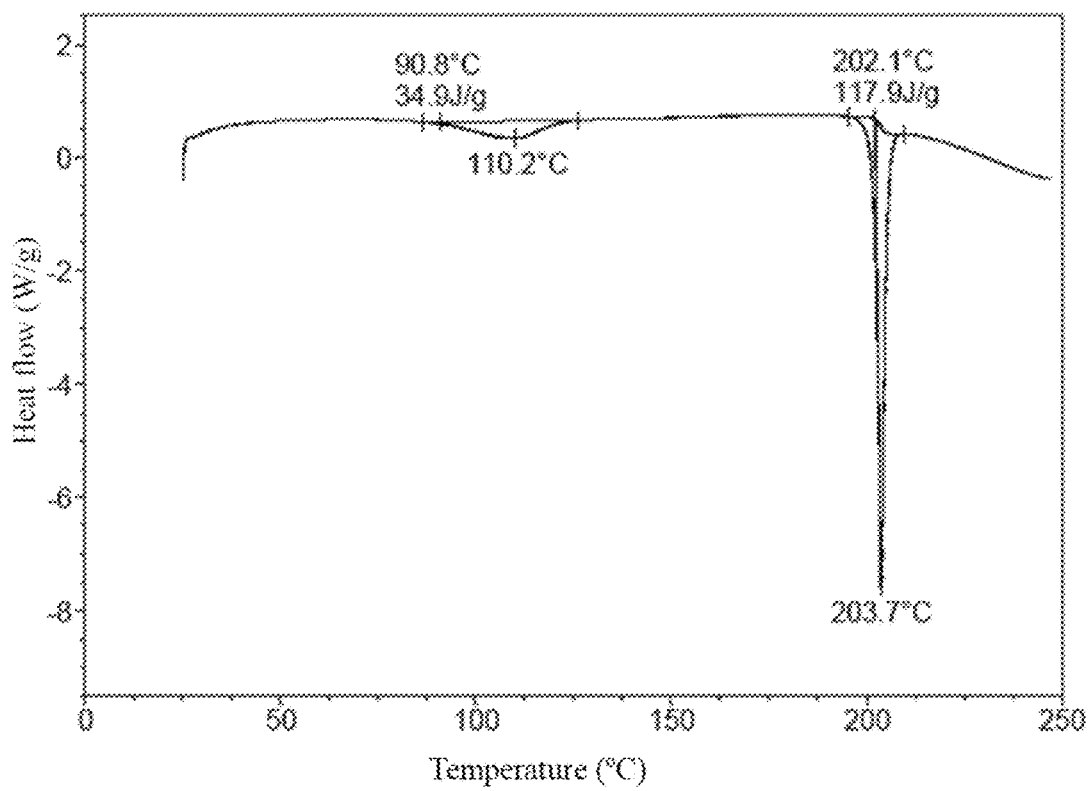
FIG. 7 shows a DSC profile of Crystal Form C.

The thermogravimetric analysis result of Crystal Form C is shown in FIG. 6, and the differential scanning calorimetry result is shown in FIG. 7. Form C had two endothermic peaks at 90.8° C. and 202.1° C. (initial temperatures). Crystal Form C had a weight loss of 2.4% when heated to 115° C. and a weight loss of 8.2% between 115° C. and 170° C.

Figure 8:
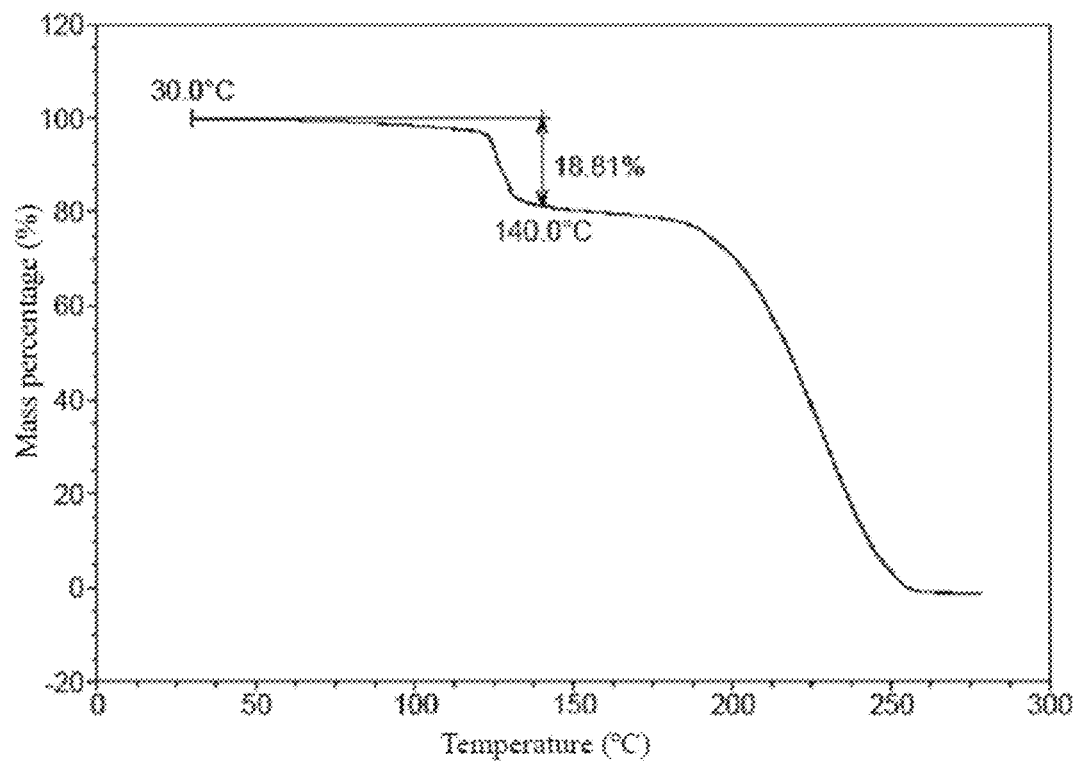
FIG. 8 shows a TGA profile of Crystal Form F.
Figure 9:
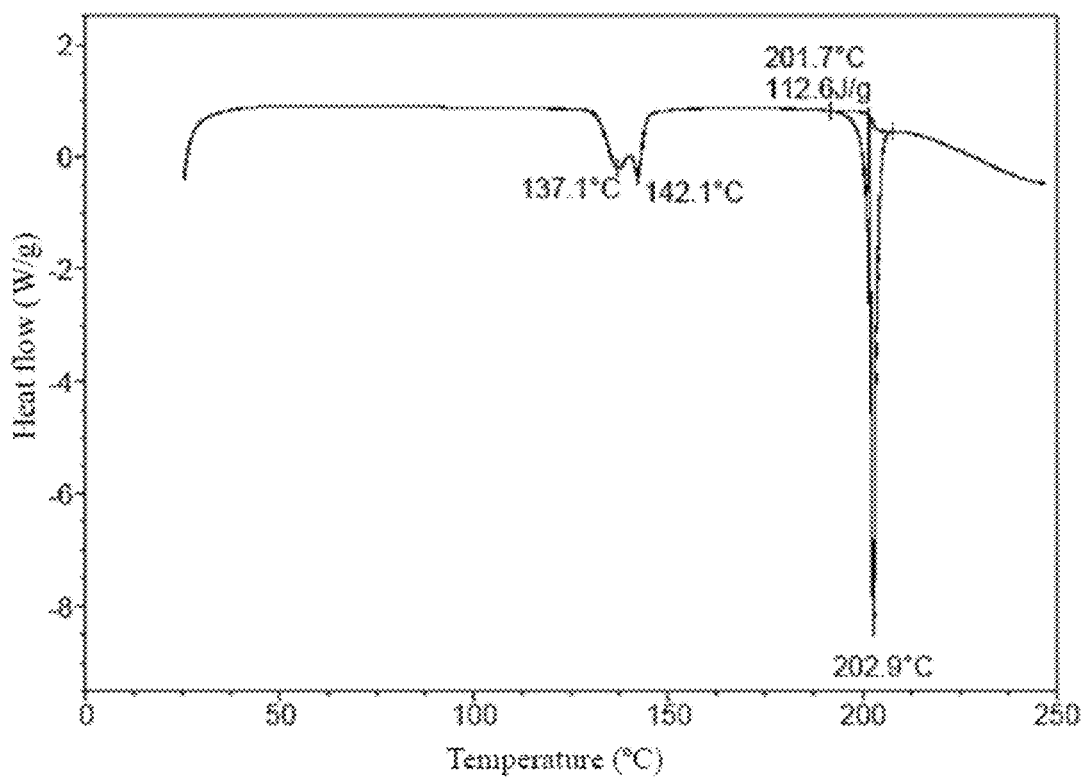
FIG. 9 shows a DSC profile of Crystal Form F.

The thermogravimetric analysis result of Crystal Form F is shown in FIG. 8, and the differential scanning calorimetry result is shown in FIG. 9. Form F had three endothermic peaks at 137.1° C., 142.1° C. (peak temperature) and 201.7° C. (initial temperature), with a significant step weight loss (19.7%) when heated to 150° C.

3. Liquid Nuclear Magnetic Hydrogen Spectrum (1H Solution NMR) Detection

Step: A liquid nuclear magnetic hydrogen spectrum was collected on a Bruker 400M nuclear magnetic resonance apparatus with DMSO-d6 as solvent.

Figure 10:
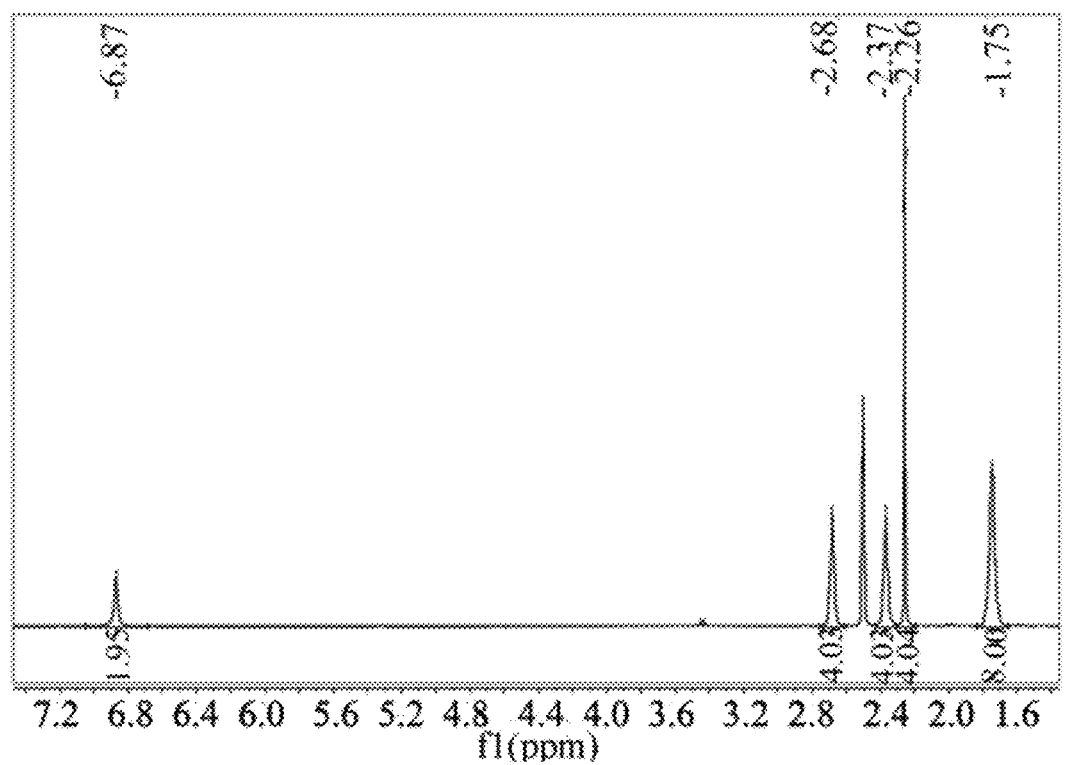
FIG. 10 shows a 1H NMR profile of Crystal Form A.

Result (1) 1H NMR of Crystal Form A is shown in FIG. 10, with a molar ratio of succinic acid to octahydroaminoacridine succinate in the sample of 1.0:1. According to the smaller TGA weight loss and the single DSC endothermic peak, Crystal Form A was supposed to be an anhydrous crystal form.

Figure 11:
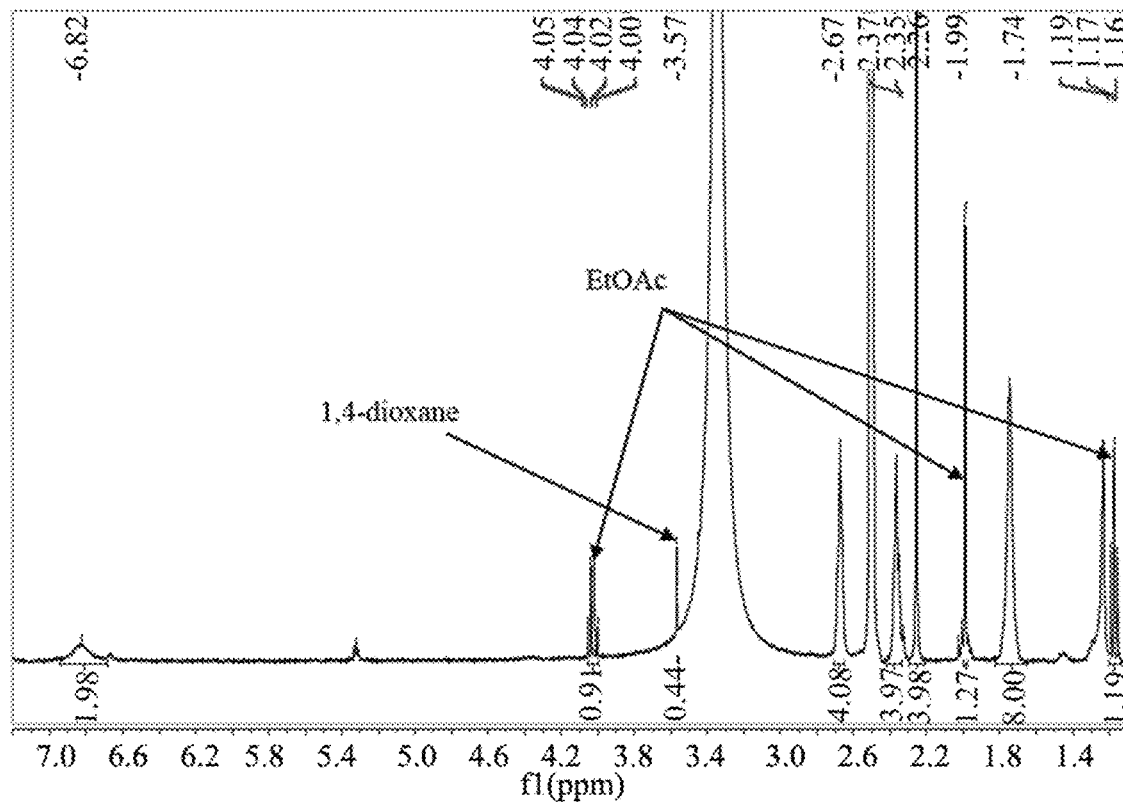
FIG. 11 shows a 1H NMR profile of Crystal Form C.
Figure 12:
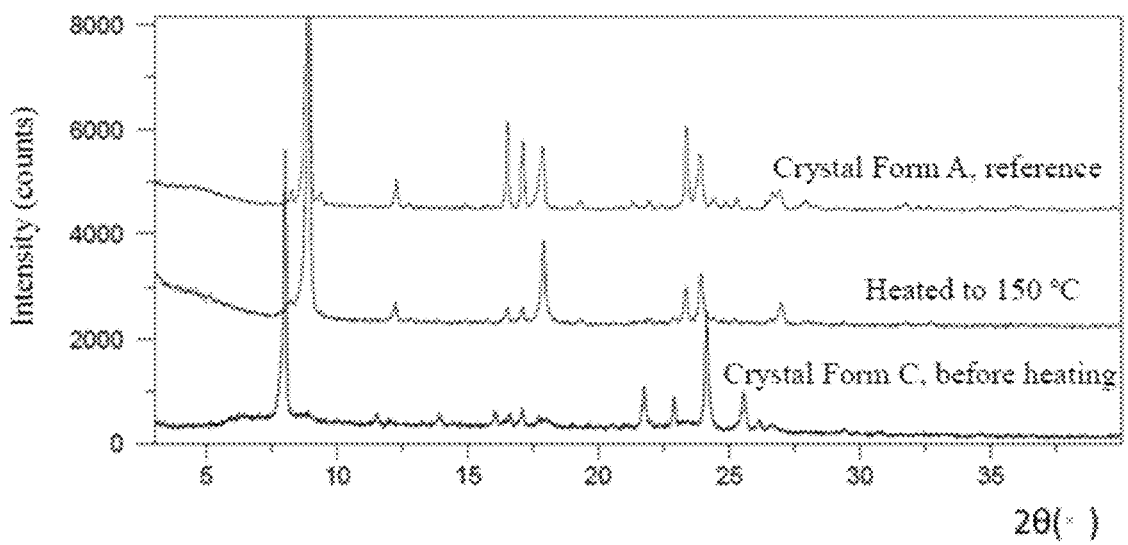
FIG. 12 shows XRPD stacked profiles of Crystal Form C before and after heating.

(2) 1H NMR of Crystal Form C is shown in FIG. 11, with a molar ratio of solvent ethyl acetate to octahydroaminoacridine succinate of 0.4:1 (9.8 wt %), and a molar ratio of 1,4-dioxane to octahydroaminoacridine succinate of 0.05:1 (1.2 wt %). To investigate the endothermic peak before the melting point, the sample of Crystal Form C was heated to 150° C., and the XRPD result (as shown in FIG. 12) showed that the sample was converted to Crystal Form A after heating. According to the above results, it was speculated that Crystal Form C was transformed into an anhydrous crystal form after the solvent was removed, indicating that the sample of Crystal Form C was an ethyl acetate solvate.

Figure 13:
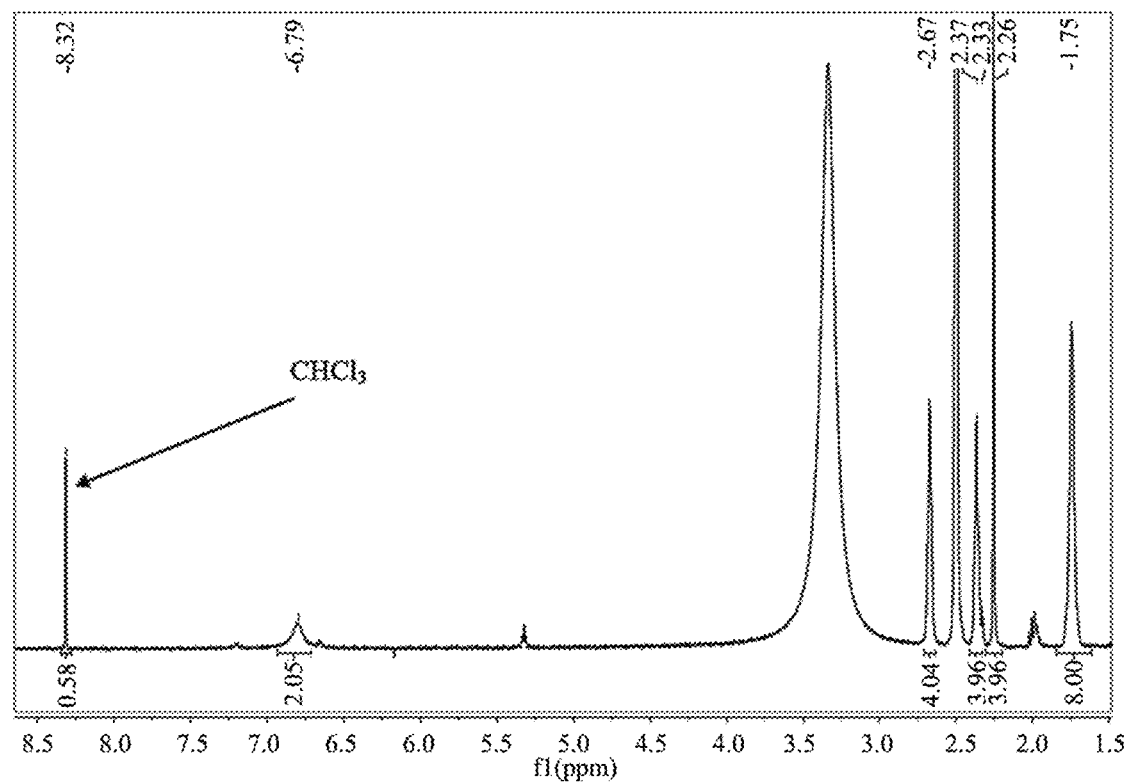
FIG. 13 shows a 1H NMR profile of Crystal Form F.
Figure 14:
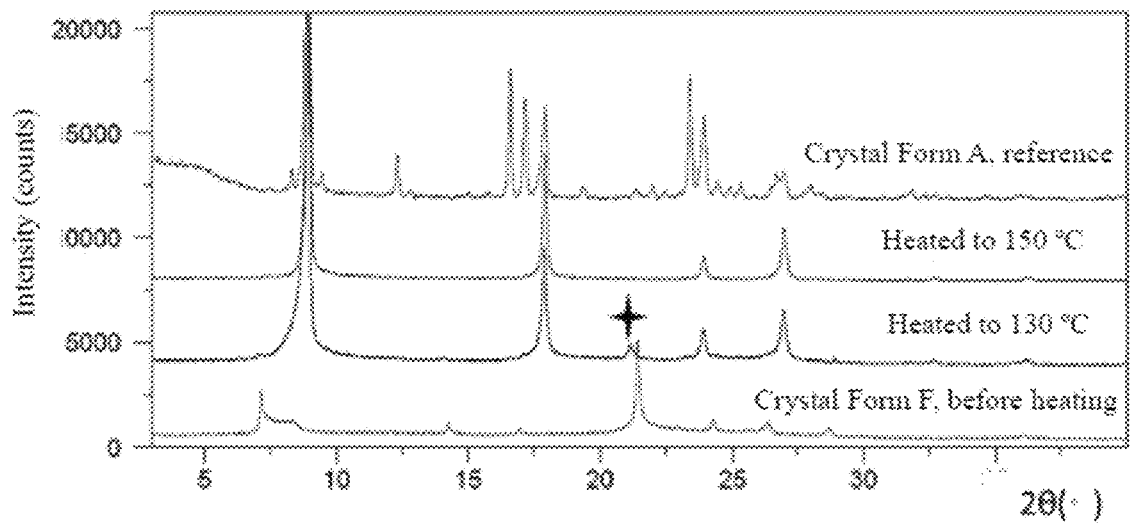
FIG. 14 shows XRPD stacked profiles of Crystal Form F before and after heating.

(3) 1H NMR of Crystal Form C is shown in FIG. 13, with a molar ratio of solvent trichloromethane to octahydroaminoacridine succinate in the sample of 0.6:1 (17.8 wt %). After the sample of Crystal Form F was heated to 130° C. and 150° C. respectively and then cooled to room temperature, the XRPD measurements were performed, and the XRPD results were shown in FIG. 14. After the sample of Crystal Form F was heated to 150° C., it was transformed into Crystal Form A (when heated to 130° C., one more diffraction peak was formed at the position of about) 21.1°. According to 1H NMR and heating test results, it was speculated that after Crystal Form F was heated, the solvent trichloromethane was removed and Crystal Form F was transformed into an anhydrous Crystal Form A, indicating that the sample of Crystal Form F was a trichloromethane solvate.

Example 3: Stability Studies on Polymorphic Forms of Octahydroaminoacridine Succinate Study on Stability of Crystal Form A:
(1) The physical and chemical stability evaluations were performed after Crystal Form A was placed in a closed condition at 80° C. for 24 hours.
(2) The physical and chemical stability evaluations were performed after Crystal Form A was placed in an open condition at 25° C./60% relative humidity and 40° C./75% relative humidity respectively for one week.

The physical and chemical stabilities of the samples were tested by XRPD and HPLC.

Figure 15:
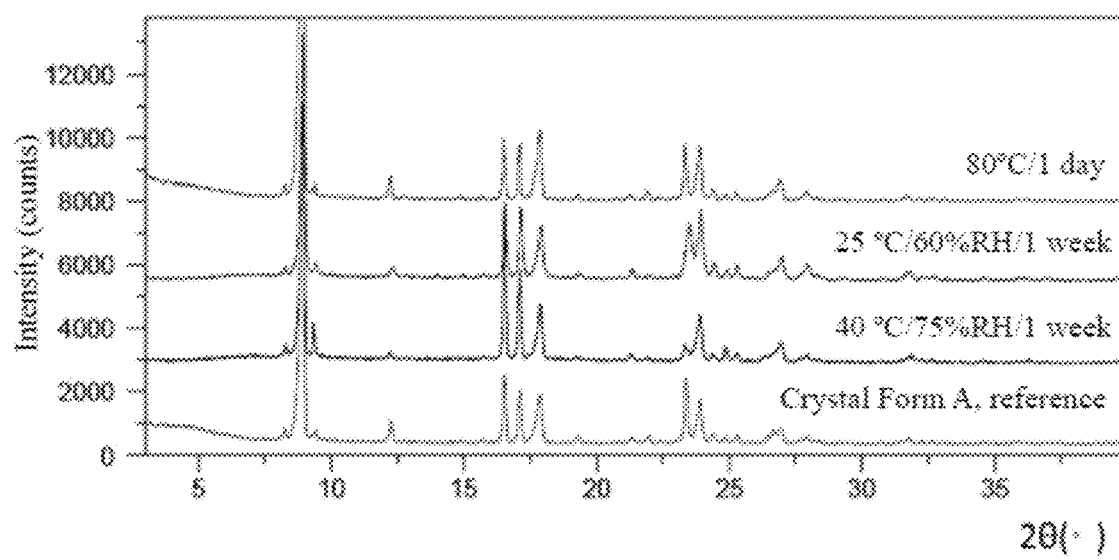
FIG. 15 shows XRPD stacked profiles of Crystal Form A before and after the stability test.

Result: the XRPD results (FIG. 15) showed that Crystal Form A was unchanged at 80° C., 25° C./60% relative humidity, and 40° C./75% relative humidity; the HPLC results showed that the chemical purity of Crystal Form A was unchanged under all three test conditions, indicating that Crystal Form A had relatively good physical and chemical stabilities.

Example 4: Study on the Equilibrium Solubility of Polymorphic Forms of Octahydroaminoacridine Succinate Determination of Equilibrium Solubility in Water
Step: 24 hours equilibrium solubility of the sample of Crystal Form A in water was tested at room temperature. In the experiment, after mixing the sample of crystal form with water to form a suspension (initial concentration was about 100 mg/mL), the stirring was carried out for 24 hours (1000 rpm) at room temperature, a supernatant obtained from the centrifugation was filtered and the solubility was measured, and the residual solid was subjected to the XRPD test.

Result

The 24 hours equilibrium solubility of Crystal Form A in $H_2O$ was 72.9 mg/mL.

Example 5: Study on the Hygroscopicity of the Polymorphic Form of Octahydroaminoacridine Succinate In order to evaluate the stability of Crystal Form A under different humidity conditions, a dynamic moisture sorption (DVS) test was carried out on the sample of Crystal Form A under the constant temperature condition of 25° C.

Result

Figure 16:
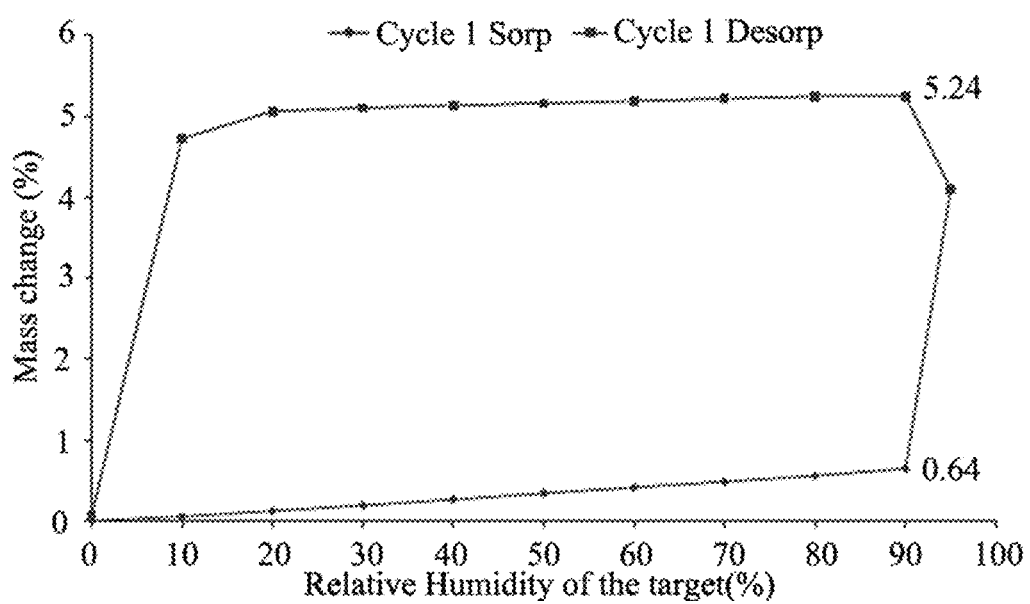
FIG. 16 shows a DVS profile of Crystal Form A.

DVS results for Crystal Form A is shown in FIG. 16, the sample begins to significantly absorb water at 90% relative humidity, and has a weight gain up to 5.2%.

Example 6: Particle Morphology Characterization

Figure 17:
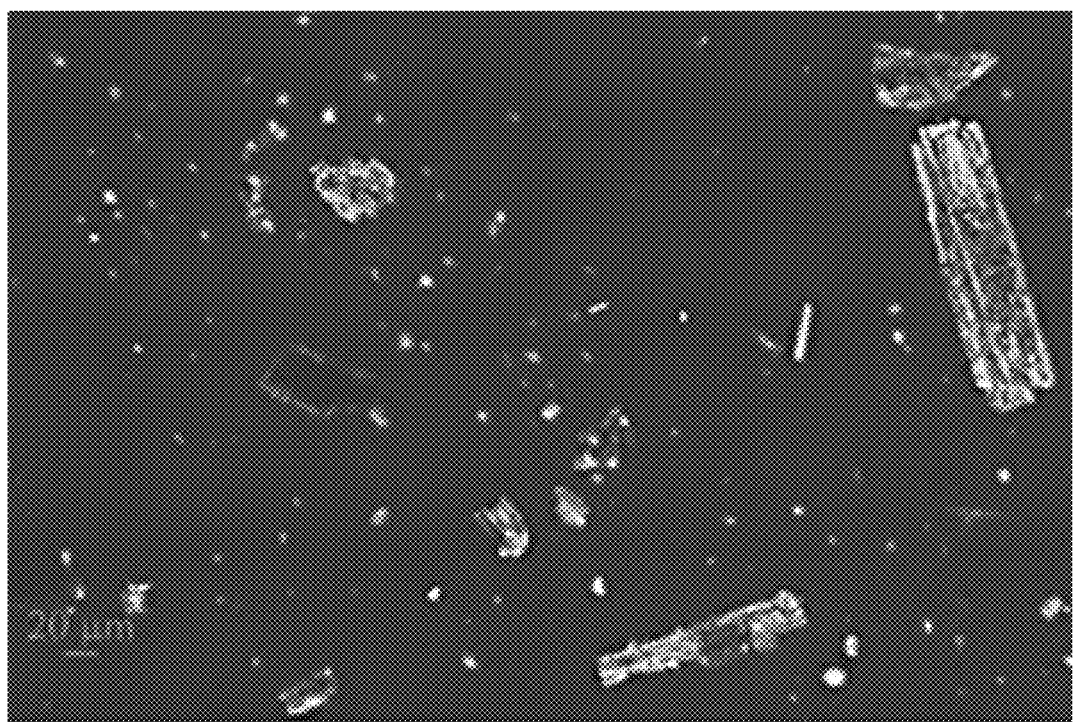
FIG. 17 shows a PLM profile of Crystal Form A.

The sample of Crystal Form A was characterized by using a polarized light microscope (PLM) and the results are shown in FIG. 17. Crystal form A was a plate crystal with the particle diameter of about 30-100 μm.

Example 7: Pharmacological Toxicology Studies of Crystal Form a

1. General Pharmacological Study

Crystal Form A of octahydroaminoacridine succinate was administered once by intragastric route at 4, 8 and 16 mg/kg, no obvious influence on the sleep number of animals with subthreshold dose of pentobarbital sodium was observed, indicating that Crystal Form A of octahydroaminoacridine succinate and pentobarbital sodium had no synergistic or antagonistic effect. For the influence on the general state, the autonomous activity and the coordinated movement of the mice, it was found that the mice in the dose groups of 4, 8, 16 mg/kg Crystal Form A of octahydroaminoacridine succinate had no abnormity in the general state, and had no obvious difference in the movement number within 5 minutes and the rate of falling from the rotating rod within 1 minute and 3 minutes compared with a normal control group, and there was no obvious difference in the general state of the mice when compared between the animals themselves before and after administration. It was hinted that Crystal Form A of octahydroaminoacridine succinate had no significant influence on the general state, autonomous activity and coordinated movement of the mice.

Meanwhile, the influence of Crystal Form A of octahydroaminoacridine succinate on the general pharmacological indexes of the normal anesthetized dog was observed. The results showed that 0.8, 1.6 and 3.2 mg/kg Crystal Form A of octahydroaminoacridine succinate had no obvious influence on the respiratory frequency, the respiratory amplitude, the arterial blood pressure, the heart rate and the electrocardiogram of the normal anesthetized dogs.

2. Toxicology Study 2.1 Acute Toxicity Study

According to the guiding principle of research on new drugs for chemical medicine, through the LD50 measurement of two animals (mouse and rat) with the intragastric administration of Crystal Form A of octahydroaminoacridine succinate, it was obtained that the LD50 for the intragastric administration of Crystal Form A of octahydroaminoacridine succinate to mouse was 66.6±3.3 mg/kg, which was approximately equivalent to 499.5 times the clinical daily dosage (8 mg/60 kg human/day) in terms of kilogram body weight; and the LD50 for the intragastric administration to rat was 109.9±9.1 mg/kg, which was approximately equivalent to 824.3 times the clinical daily dosage (8 mg/60 kg human/day) in terms of kilogram body weight.

2.2 Long Term Toxicity Study

This experiment was conducted to study the long-term toxicity test for the intragastric administration of Crystal Form A of octahydroaminoacridine succinate to the rodent rats. The test was divided into a low-dose group (7.5 mg/kg), a medium-dose group (15 mg/kg), a high-dose group (30 mg/kg) and a blank control group (distilled water). 120 Wistar rats were used, 30 rats per group, wherein half of them were males and half were females. The administration route was ig administration, once per day, 6-day administration per week, and a 27-week test period. Approximately ⅓ animals were observed for 2-week recovery period changes in each experimental group. General condition, body weight changes, blood cytological and biochemical indications, gross anatomy and histopathological examination of animals were observed as required by long-term toxicity testing of chemical drugs.

The results showed that after the rats were continuously administrated through the intragastric route with 7.5, 15 and 30 mg/kg of Crystal Form A of octahydroaminoacridine succinate (which were 56.3, 112.5 and 225 times the clinical maximum daily dosage of 8 mg/60 kg human/day respectively in term of the weight) for 27 weeks, the general state, the behavioral activity, the mental state, the fur, the urine and feces, and the food (water) intake of the tested animals were all normal. The indexes of electrocardiogram PR interval, QRS interval, QT interval, T wave, heart rate and the like of each administration group had no significant difference compared with those of the control group. The weight of the male rats in the high-dose group was obviously reduced between 20 and 27 weeks of the administration and significantly different compared with that of the control group ($p<0.05$ or $p<0.01$), the weight of the female rats in the high-dose group was obviously reduced between 20 and 27 weeks of the administration and significantly different compared with that of the control group ($p<0.05$), and 5 animals died. The body weights of both male and female rats in the recovery period were completely recovered, and no obvious difference was found compared with the control group. Although there was no obvious difference in hematology, blood biochemistry examination and each organ coefficient compared with the control group, 2 rats with obvious elevation of the liver function index ALT were found 3 months and 6 months after the administration in the high-dose group. No obvious pathological changes caused by the drug toxicity were found in the general examination and the microscopic examination of all organs. After stopping the administration for 2 weeks, each laboratory examinations and each organ coefficients were all normal in each group, and no obvious drug-damaged pathological changes were found in pathological examination of each organ under naked eyes examination and light microscope examination in each group.

Under the test condition, for 30 mg/kg of the tested substance, the body weight could be obviously reduced, a part of animals had ALT (liver function index) abnormality and a part of animals died, but no obvious drug-damaged pathological changes appeared in the liver. After stopping the administration for 2 weeks, the reduced weight and the abnormal liver function index ALT appeared in the animals were all recovered, and no animals died. It was indicated that the toxic target organ for the long-term administration of Crystal Form A of octahydroaminoacridine succinate could be the liver, but reversible. The non-toxic reaction dose was 15 mg/kg.

Example 8: Drug Effect Study of Crystal Form A

Figure 18:
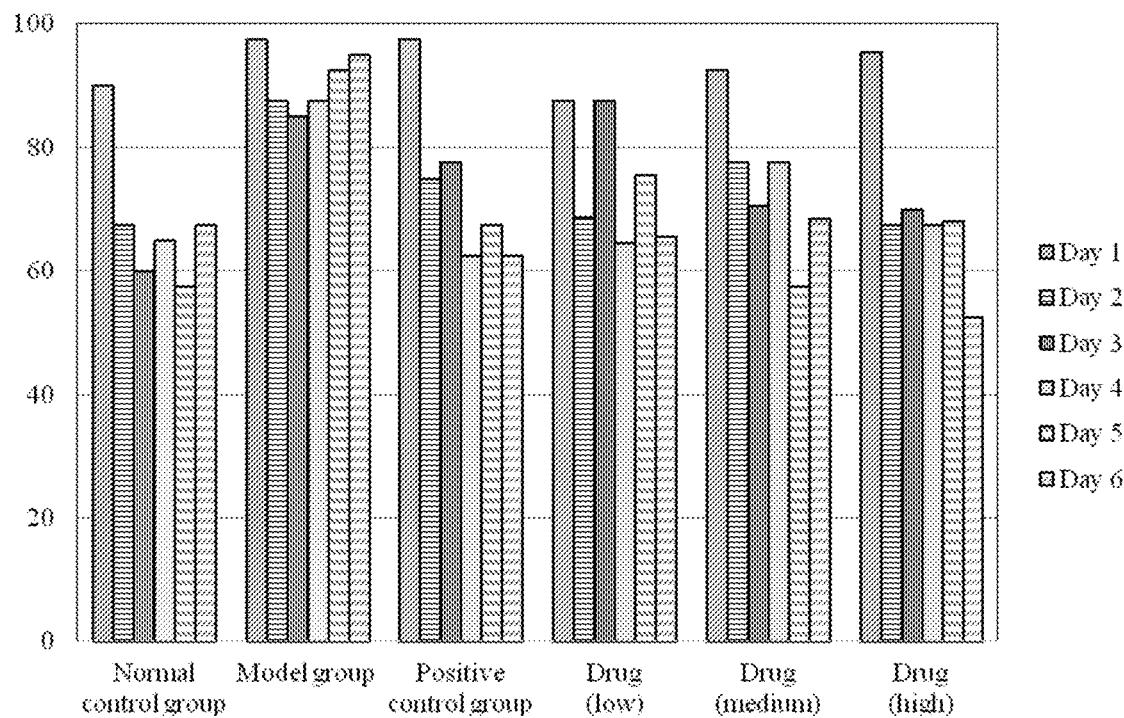
FIG. 18 shows the effect of Crystal Form A on the strategy for reaching the platform of β-amyloid induced dementia rats (peripheral and random)

1. Therapeutic Effect on Beta-Amyloid Induced Senile Dementia
(1) Animals
100 male Wistar rats with the weight of 280-320 g, provided by the Changchun High and New Medicine Experiment Animal Center, and the qualification number: 10-5113.
(2) Test Method
A rat senile dementia model was established according to the references [CONG Wei-Hong, LIU Jian-Xun. Progress in the study of animal models of Alzheimer's disease, Chinese Pharmacological Bulletin, 2003; 19 (5): 497-501; SHEN Yu-Xian, YANG Jun, WEI wei, et al., Learning and memory dysfunction in rats induced by beta-amyloid peptide fragment 25-35, Chinese Pharmacological Bulletin, 2001, 17 (1): 26-19; LIN Yu, CHEN Junpao, XU Bin, et al. Study of rats with beta-amyloid injection into hippocampus to establish a memory impairment model, Chin J Psychiatry, 2000, 33 (4): 222-225]. 100 mg/kg of ketamine was used for anesthetizing a rat, the anesthetized rat was fixed on a stereotaxic instrument, a fixing plane was adjusted to enable the incisor teeth to be 2 mm lower than the middle point of the connecting line of the inner ears, the skin at the top of the head was cleaned and a middle vertical incision was made, the subcutaneous fascia was stripped to expose the parietal bone, small holes were drilled behind coronal sutures on both sides, the broken bone fragments were taken out, and the integrity of the dura mater was maintained. Hippocampal region location coordinates: 3.5 mm posterior to bregma, 2.0 mm lateral to midline, and 2.7 mm below endocranium. Aβ 25-35 of 5 μL (10 μg) aggregated peptide was injected into each side by a micro-injector respectively, the injection was completed within 5 minutes, and the needle was left for 5 minutes after the injection so as to avoid the overflow of the medicine when the needle was pulled out. The normal control group was operated in the same manner and injected with the same volume of saline. After the operation, the dental base acrylic resin powder was used to seal the hole on the cranial bone and the skin was sutured, 100,000 units penicillin G was intramuscularly injected per day within three days for anti-infection, and the animals were divided into groups on the third day after operation and the administration was started. The normal control group and the model group were administrated through the intragastric route with distilled water by 0.5 ml/100 g, the positive control group was administrated through the intragastric route with donepezil hydrochloride by 1.75 mg/kg (equivalent to 3.85 times the clinical daily dosage of 5 mg/70 kg), the low, medium and high-dose groups of Crystal Form A of octahydroaminoacridine succinate were administrated through the intragastric route with Crystal Form A of octahydroaminoacridine succinate by 0.7, 1.4 and 2.8 mg/kg (equivalent to 0.96, 1.92 and 3.85 times the clinical daily dosage of 8 mg/70 kg) respectively. The water maze test and the step-down test were carried out after continuous administration for 7 days, and the administration was continued during the test period. The water maze test was continuously performed for 7 days, in the first 6 days, in four different water entry points of quadrants 1, 2, 3 and 4, the time, the swimming path length, the orientation angle and the average speed of the rat reaching the platform were measured, meanwhile, the strategy for reaching the platform adopted by rats was observed, on the 7th day, the platform was removed, the number of rats crossing the platform in 2 minutes, the residence time in the platform area, the residence time in the platform quadrants, the percentage of the swimming path length in the platform area quadrants to the total swimming path length, the average speed and the orientation angle were measured. After the water maze test was finished, the step-down test was performed, and the number of electric shocks (or called as the error number) received by each rat within 5 minutes was recorded as the learning performance. The test was performed again after 24 hours, namely, the memory retention test, and the latent period for stepping-down the platform for the first time and the total error number in five minutes were recorded. After the step-down test was finished, the brain was taken quickly for pathological examination, and the pathological changes of the hippocampus and the cortex were observed.
(3) Test Results
Compared with the normal control group, for the rats in the model group, on Day 2 to Day 6, the latent period for reaching the platform was obviously prolonged (P<0.05 or P<0.01), on Day 3 to Day 6, the swimming path length for reaching the platform was obviously prolonged (P<0.05), on Day 2 and Day 5, the orientation angle was obviously increased (P<0.05 or P<0.01), on Day 1, Day 3, and Day 5, the swimming speed was obviously reduced (P<0.05), on Day 7, the number of crossing the platform within 2 minutes and the residence time in the platform area of rats were obviously reduced (P<0.05 or P<0.01), the residence time in the platform quadrants, the percentage of the swimming path length in the platform area quadrants to the total swimming path length, the average speed and the orientation angle of rats were not obviously changed, the conversion from the peripheral type and the random type to the tendency type and the linear type in the strategy for looking for the platform was obviously slowed down (P<0.05 or P<0.01), on Day 1 and Day 2, the step-down error number was obviously increased (P<0.05), on Day 2, the error latency was obviously shortened (P<0.05); compared with the model group, for the rats in the dose group of 1.4 mg/kg Crystal Form A of octahydroaminoacridine succinate in the water maze, on Day 1 to Day 6, the latent period for reaching the platform was obviously shortened (P<0.05 or P<0.01), for the rats in the dose group of 2.8 mg/kg Crystal Form A of octahydroaminoacridine succinate in the water maze, on Day 2 to Day 6, the latent period for reaching the platform was obviously shortened (P<0.05 or P<0.01), for the rats in the dose group of 0.7 mg/kg Crystal Form A of octahydroaminoacridine succinate in the water maze, on Day 1, the latent period for reaching the platform was obviously shortened (P<0.05), for the dose group of 1.4 mg/kg Crystal Form A of octahydroaminoacridine succinate, on Day 3 and Day 5, the swimming path length for reaching the platform was obviously shortened (P<0.05), for the dose group of 2.8 mg/kg Crystal Form A of octahydroaminoacridine succinate, on Day 5 and Day 6, the swimming path length for reaching the platform was obviously shortened (P<0.05), for the dose groups of 0.7 and 1.4 mg/kg Crystal Form A of octahydroaminoacridine succinate, on Day 2, the orientation angle was obviously decreased (P<0.05), for the dose group of 2.8 mg/kg Crystal Form A of octahydroaminoacridine succinate, on Day 2, Day 3, Day 5 and Day 6, the orientation angle was obviously decreased (P<0.05 or P<0.01), for the dose groups of 0.7, 1.4 and 2.8 mg/kg Crystal Form A of octahydroaminoacridine succinate, on Day 1, the swimming speed was obviously increased (P<0.05), for the dose groups of 0.7, 1.4 and 2.8 mg/kg Crystal Form A of octahydroaminoacridine succinate, on Day 7, the number of rats crossing the platform within 2 minutes, and the residence time on the platform were obviously increased (P<0.05 or P<0.01), for the dose group of 1.4 mg/kg Crystal Form A of octahydroaminoacridine succinate, the residence time in the platform quadrants, and the percentage of the swimming path length in the platform area quadrants to the total swimming path length were obviously increased (P<0.05), for the dose groups of 0.7, 1.4 and 2.8 mg/kg Crystal Form A of octahydroaminoacridine succinate, the average speed and the orientation angle were not obviously changed, for the dose groups of 0.7, 1.4 and 2.8 mg/kg Crystal Form A of octahydroaminoacridine succinate, the conversion from the peripheral type and the random type to the tendency type and the linear type in the strategy for looking for the platform was obviously increased (P<0.05 or P<0.01), for the dose group of 2.8 mg/kg Crystal Form A of octahydroaminoacridine succinate, on Day 1 and Day 2 the step-down error number was obviously reduced (P<0.05), and on Day 2, the error latency was obviously prolonged (P<0.05), for the rats in the positive control Group in the water maze, on Day 1 to Day 6, there was a shortened trend in the latent period for reaching the platform, but no statistical significance, on Day 4, the swimming path length for reaching the platform was obviously shortened (P<0.05), on Day 2, the orientation angle was obviously decreased (P<0.05), on Day 1 to Day 6, the swimming speed was not obviously changed, on Day 7, the residence time in the platform quadrants within 2 minutes of rats, the number of crossing the platform, the residence time in the platform area and the percentage of the swimming path length in the platform area quadrants to the total swimming path length were obviously increased (P<0.05), the average speed and the orientation angle of rats were not obviously changed, the conversion from the peripheral type and the random type to the tendency type and the linear type in the strategy for looking for the platform was obviously increased (P<0.05 or P<0.01), on Day 1 and Day 2 the step-down error number was obviously reduced (P<0.05), on Day 2, the error latency was obviously prolonged (P<0.05). Pathological findings: low and medium-dose groups of Crystal Form A of octahydroaminoacridine succinate: a slightly reduced number and an uneven arrangement of cortical nerve cells, visible nuclear pyknosis, deeply stained necrotic nerve cells, more neurotropic phenomena. The number of hippocampal nerve cells was reduced, more neurotropic phenomena was occurred, and compared with the model group, there was no obvious difference in the pathological changes of cortex and hippocampus. High-dose group of Crystal Form A of octahydroaminoacridine succinate: a large number and uniform arrangement of cortical nerve cells, nuclear pyknosis, less deeply stained necrotic nerve cells, occasional occurrence of neurotropic cellular phenomenon, regular arrangement and clear level of hippocampal nerve cells, no obvious reduction of nerve cell number, and occasional occurrence of necrotic nerve cells. The high-dose group of Crystal Form A of octahydroaminoacridine succinate could relieve the pathological damage of cerebral cortex and hippocampus of rats caused by beta-amyloid, and the results are shown in Tables 15-19 and FIG. 18.

TABLE 15

Influence of Crystal Form A and Crystal Form K on the time (s) for the rats with beta-amyloid induced senile dementia reaching the platform (x ± s)

| Groups | n | Day 1 | Day 2 | Day 3 |
|---|---|---|---|---|
| Normal control group | 10 | 65.28 ± 25.42 | 28.27 ± 16.39* | 17.43 ± 12.73* |
| Model group | 10 | 80.44 ± 25.24 | 54.35 ± 31.72 | 40.74 ± 26.98 |
| Positive control group | 10 | 72.43 ± 30.97 | 38.98 ± 33.812 | 34.41 ± 37.35 |
| Crystal Form A | | | | |
| 0.7 mg/kg | 8 | 51.79 ± 26.01* | 29.20 ± 28.52 | 39.88 ± 39.00 |
| 1.4 mg/kg | 10 | 47.00 ± 19.96* | 29.60 ± 18.83* | 15.74 ± 5.83* |
| 2.8 mg/kg | 10 | 65.22 ± 26.94 | 27.92 ± 18.96* | 20.24 ± 10.26* |
| Crystal Form K | | | | |
| 0.7 mg/kg | 10 | 70.00 ± 14.73 | 48.50 ± 15.28 | 41.80 ± 11.68 |
| 1.4 mg/kg | 10 | 70.50 ± 14.60 | 51.60 ± 17.26 | 53.40 ± 23.24 |
| 2.8 mg/kg | 10 | 66.90 ± 11.45 | 50.40 ± 17.10 | 40.50 ± 20.47 |
| Groups | n | Day 4 | Day 5 | Day 6 |
| Normal control group | 10 | 14.92 ± 9.89** | 15.44 ± 17.56** | 15.05 ± 8.61** |
| Model group | 10 | 53.33 ± 40.51 | 48.40 ± 25.16 | 48.99 ± 35.32 |
| Positive control group | 10 | 29.32 ± 39.89 | 29.16 ± 24.95 | 28.99 ± 35.61 |
| Crystal Form A | | | | |
| 0.7 mg/kg | 8 | 32.05 ± 39.88 | 25.95 ± 33.84 | 21.76 ± 23.11 |
| 1.4 mg/kg | 10 | 20.82 ± 11.32* | 14.95 ± 9.19** | 20.62 ± 22.63* |
| 2.8 mg/kg | 10 | 22.73 ± 21.88* | 14.17 ± 11.56** | 10.70 ± 6.74** |

TABLE 15-continued

Influence of Crystal Form A and Crystal Form K on the time (s) for the
rats with beta-amyloid induced senile dementia reaching the platform (x ± s)

Crystal Form K

| | | | | |
|---|---|---|---|---|
| 0.7 mg/kg | 10 | 38.10 ± 22.41 | 36.20 ± 27.16 | 35.90 ± 24.22 |
| 1.4 mg/kg | 10 | 36.00 ± 20.42 | 33.50 ± 21.95 | 38.90 ± 22.26 |
| 2.8 mg/kg | 10 | 37.00 ± 17.54 | 30.10 ± 15.85 | 36.10 ± 22.34 |

Compared with the model group:
*P < 0.05,
**P < 0.01

TABLE 16

Influence of Crystal Form A and Crystal Form K on the swimming path length (cm)
for the rats with beta-amyloid induced senile dementia reaching the platform (x ± s)

| Groups | n | Day 1 | Day 2 | Day 3 |
|---|---|---|---|---|
| Normal control group | 10 | 1324.75 ± 547.17 | 667.51 ± 492.33 | 394.08 ± 263.20* |
| Model group | 10 | 1227.37 ± 417.67 | 935.48 ± 452.32 | 802.52 ± 610.68 |
| Positive control group | 10 | 1029.43 ± 453.12 | 762.34 ± 562.06 | 572.83 ± 576.82 |
| Crystal Form A | | | | |
| 0.7 mg/kg | 8 | 1169.52 ± 985.73 | 762.15 ± 878.65 | 922.69 ± 927.53 |
| 1.4 mg/kg | 10 | 1022.59 ± 558.57 | 657.63 ± 419.44 | 359.75 ± 164.16* |
| 2.8 mg/kg | 10 | 1215.28 ± 534.19 | 717.16 ± 484.50 | 426.44 ± 213.56 |
| Crystal Form K | | | | |
| 0.7 mg/kg | 10 | 1196.20 ± 260.35 | 796.10 ± 179.65 | 760.80 ± 277.08 |
| 1.4 mg/kg | 10 | 1151.50 ± 313.31 | 772.80 ± 229.71 | 737.60 ± 223.46 |
| 2.8 mg/kg | 10 | 1188.50 ± 273.99 | 770.70 ± 248.67 | 584.50 ± 181.92 |

| Groups | n | Day 4 | Day 5 | Day 6 |
|---|---|---|---|---|
| Normal control group | 10 | 374.89 ± 332.21* | 327.81 ± 360.87* | 330.14 ± 173.95* |
| Model group | 10 | 1042.95 ± 910.83 | 900.57 ± 766.93 | 992.00 ± 895.33 |
| Positive control group | 10 | 312.04 ± 316.86* | 495.72 ± 380.99 | 413.33 ± 483.35 |
| Crystal Form A | | | | |
| 0.7 mg/kg | 8 | 806.38 ± 1014.62 | 571.38 ± 716.43 | 461.68 ± 417.67 |
| 1.4 mg/kg | 10 | 493.65 ± 256.60 | 278.26 ± 125.79* | 402.97 ± 434.93 |
| 2.8 mg/kg | 10 | 600.43 ± 563.07 | 312.55 ± 230.50* | 252.87 ± 161.30* |
| Crystal Form K | | | | |
| 0.7 mg/kg | 10 | 685.10 ± 319.17 | 563.90 ± 154.71 | 513.30 ± 194.29 |
| 1.4 mg/kg | 10 | 653.50 ± 321.17 | 562.80 ± 280.10 | 523.30 ± 182.50 |
| 2.8 mg/kg | 10 | 544.70 ± 179.35 | 481.50 ± 203.96 | 540.50 ± 166.77 |

Compared with the model group:
*P < 0.05,
**P < 0.01

TABLE 17

Influence of Crystal Form A and Crystal
Form K on the orientation angle (°) for the rats with
beta-amyloid induced senile dementia reaching the platform (x ± s)

| Groups | n | Day 1 | Day 2 | Day 3 |
|---|---|---|---|---|
| Normal control group | 10 | 67.15 ± 39.04 | 46.38 ± 24.62* | 47.05 ± 20.82 |
| Model group | 10 | 68.32 ± 15.60 | 69.46 ± 10.75 | 56.43 ± 11.98 |
| Positive control group | 10 | 75.41 ± 22.31 | 50.14 ± 23.02* | 52.85 ± 27.04 |
| Crystal Form A | | | | |
| 0.7 mg/kg | 8 | 62.79 ± 19.80 | 48.33 ± 25.33* | 59.46 ± 34.15 |
| 1.4 mg/kg | 10 | 77.42 ± 21.94 | 53.95 ± 19.36* | 49.79 ± 16.12 |
| 2.8 mg/kg | 10 | 61.45 ± 13.71 | 42.58 ± 17.57** | 41.19 ± 18.30* |

TABLE 17-continued

Influence of Crystal Form A and Crystal
Form K on the orientation angle (°) for the rats with
beta-amyloid induced senile dementia reaching the platform (x ± s)

Crystal Form K

| | | | | |
|---|---|---|---|---|
| 0.7 mg/kg | 10 | 72.32 ± 21.32 | 62.15 ± 19.37 | 58.23 ± 27.90 |
| 1.4 mg/kg | 10 | 71.28 ± 13.47 | 63.27 ± 10.38 | 54.77 ± 18.42 |
| 2.8 mg/kg | 10 | 68.37 ± 20.14 | 66.21 ± 18.35 | 52.93 ± 17.44 |

| Groups | n | Day 4 | Day 5 | Day 6 |
|---|---|---|---|---|
| Normal control group | 10 | 40.11 ± 19.08 | 42.43 ± 18.70** | 45.39 ± 21.64 |
| Model group | 10 | 59.98 ± 30.19 | 66.65 ± 12.39 | 63.53 ± 21.07 |
| Positive control group | 10 | 46.37 ± 17.86 | 50.54 ± 24.98 | 44.21 ± 34.00 |

TABLE 17-continued

Influence of Crystal Form A and Crystal Form K on the orientation angle (°) for the rats with beta-amyloid induced senile dementia reaching the platform (x ± s)

Crystal Form A

| | | | | |
|---|---|---|---|---|
| 0.7 mg/kg | 8 | 47.21 ± 18.21 | 54.72 ± 24.68 | 46.47 ± 18.69 |
| 1.4 mg/kg | 10 | 53.54 ± 25.57 | 53.41 ± 23.18 | 46.29 ± 22.64 |
| 2.8 mg/kg | 10 | 47.22 ± 23.29 | 43.23 ± 15.80* | 40.91 ± 15.25* |

Crystal Form K

| | | | | |
|---|---|---|---|---|
| 0.7 mg/kg | 10 | 57.32 ± 31.22 | 54.22 ± 28.34 | 52.11 ± 22.00 |
| 1.4 mg/kg | 10 | 51.48 ± 11.38 | 53.62 ± 17.88 | 50.65 ± 18.77 |
| 2.8 mg/kg | 10 | 50.22 ± 18.92 | 51.22 ± 20.11 | 48.78 ± 16.83 |

Compared with the model group:
*P < 0.05,
**P < 0.01

TABLE 18

Influence of Crystal Form A and Crystal Form K on the speed (cm/s) for the rats with beta-amyloid induced senile dementia reaching the platform (x ± s)

| Groups | n | Day 1 | Day 2 | Day 3 |
|---|---|---|---|---|
| Normal control group | 10 | 22.77 ± 8.29* | 24.30 ± 6.42 | 26.10 ± 4.82* |
| Model group | 10 | 15.74 ± 3.94 | 20.14 ± 7.32 | 20.58 ± 5.13 |
| Positive control group | 10 | 16.03 ± 4.22 | 20.78 ± 5.83 | 19.15 ± 4.64 |
| Crystal Form A | | | | |
| 0.7 mg/kg | 8 | 22.41 ± 7.84* | 28.34 ± 10.42 | 25.56 ± 10.30 |
| 1.4 mg/kg | 10 | 21.16 ± 5.82* | 24.65 ± 5.95 | 23.53 ± 5.74 |
| 2.8 mg/kg | 10 | 19.76 ± 2.88* | 23.62 ± 5.04 | 22.47 ± 2.59 |
| Crystal Form K | | | | |
| 0.7 mg/kg | 10 | 18.56 ± 4.91 | 19.44 ± 9.85 | 19.76 ± 10.49 |
| 1.4 mg/kg | 10 | 18.24 ± 6.88 | 20.42 ± 7.24 | 20.07 ± 7.36 |
| 2.8 mg/kg | 10 | 19.42 ± 5.93 | 20.89 ± 6.68 | 20.00 ± 8.73 |

| Groups | n | Day 4 | Day 5 | Day 6 |
|---|---|---|---|---|
| Normal control group | 10 | 27.16 ± 5.26 | 24.28 ± 4.50* | 23.17 ± 3.64 |
| Model group | 10 | 22.97 ± 5.58 | 19.85 ± 4.46 | 22.21 ± 7.14 |
| Positive control group | 10 | 22.07 ± 8.05 | 19.67 ± 3.94 | 18.28 ± 5.12 |
| Crystal Form A | | | | |
| 0.7 mg/kg | 8 | 24.92 ± 2.52 | 27.17 ± 13.51 | 23.50 ± 9.00 |
| 1.4 mg/kg | 10 | 25.56 ± 4.54 | 20.14 ± 4.25 | 20.87 ± 4.35 |
| 2.8 mg/kg | 10 | 27.31 ± 4.62 | 23.96 ± 4.94 | 24.73 ± 4.83 |
| Crystal Form K | | | | |
| 0.7 mg/kg | 10 | 22.17 ± 13.09 | 21.30 ± 9.86 | 21.55 ± 6.47 |
| 1.4 mg/kg | 10 | 20.53 ± 11.21 | 22.73 ± 17.69 | 20.62 ± 7.36 |
| 2.8 mg/kg | 10 | 21.48 ± 9.09 | 21.90 ± 10.66 | 18.52 ± 7.78 |

Compared with the model group:
*P < 0.05,
**P < 0.01

TABLE 19

Influence of Crystal Form A and Crystal Form K on the adopted strategy for the rats with beta-amyloid induced senile dementia reaching the platform (the peripheral type and the random type %)

| Groups | n | Day 1 | Day 2 | Day 3 | Day 4 | Day 5 | Day 6 |
|---|---|---|---|---|---|---|---|
| Normal control group | 10 | 90.00 | 67.50* | 60.00* | 65.00* | 57.50** | 67.50 |
| Model group | 10 | 97.50 | 87.50 | 85.00 | 87.50 | 92.50 | 95.00 |
| Positive control group | 10 | 97.50 | 75.00 | 77.50 | 62.50** | 67.50** | 62.50* |
| Crystal Form A | | | | | | | |
| 0.7 mg/kg | 8 | 87.50 | 68.75 | 87.50 | 64.50* | 75.50* | 65.50 |
| 1.4 mg/kg | 10 | 92.50 | 77.50 | 70.50 | 77.50 | 57.50* | 68.50 |
| 2.8 mg/kg | 10 | 95.50 | 67.50* | 70.00 | 67.50* | 68.00** | 52.50** |
| Crystal Form K | | | | | | | |
| 0.7 mg/kg | 10 | 95.24 | 79.34 | 80.31 | 70.66 | 71.53 | 68.55 |
| 1.4 mg/kg | 10 | 94.82 | 78.13 | 77.37 | 71.34 | 69.33 | 65.72 |
| 2.8 mg/kg | 10 | 93.17 | 80.67 | 75.48 | 68.99 | 67.59 | 60.14 |

Compared with the model group: * P < 0.05, **P < 0.01

2. Therapeutic Effect on Common Carotid Artery Occlusion-Induced Vascular Dementia (1) Animals 100 male Wistar rats with the weight of 350-400 g, provided by the Changchun High and New Medicine Experiment Animal Center, and the qualification number: 10-5113.

(2) Test Method

A rat blood vessel dementia model was made according to the references [ZHAO Xian-lin, FANG Xiu-bin, LI Dong-pei. Establishment of Vascular Dementia Model in Rats, J Chin Med Univ, 2002, 31 (3): 166-168; WANG Yong-yan, Zhang Bo-li, Editor-in-chief. Modern Chinese Medicine Clinic and Research on Vascular Dementia, People's Medical Publishing House, October 2003, First Version 214]: Chloral hydrate 0.4 g/kg was intraperitoneally injected for anesthetizing rats, and bilateral common carotid arteries were isolated and ligated. The animals were fed for 16 weeks, divided into groups on the last 7 days, and administered. The normal control group and the model group were administrated through the intragastric route with distilled water by 0.5 ml/100 g, the positive control group was administrated through the intragastric route with donepezil hydrochloride by 1.75 mg/kg (equivalent to 3.85 times the clinical daily dosage of 5 mg/70 kg), the low, medium and high-dose groups of Crystal Form A of octahydroaminoacridine succinate were administrated through the intragastric route with Crystal Form A of octahydroaminoacridine succinate by 0.7, 1.4 and 2.8 mg/kg (equivalent to 0.96, 1.92 and 3.85 times the clinical daily dosage of 8 mg/70 kg). The water maze test and the step-down test were carried out after continuous administration for 7 days, and the administration was continued during the test period. The water maze test was continuously performed for 7 days, in the first 6 days, in four different water entry points of quadrants 1, 2, 3 and 4, the time, the swimming path length, the orientation angle and the average speed of the rat reaching the platform were measured, meanwhile, the strategy for reaching the platform adopted by rats was observed, on the 7th day, the platform was removed, the number of rats crossing the platform in 2 minutes, the residence time in the platform area, the residence time in the platform quadrants, the percentage of the swimming path length in the platform area quadrants to the total swimming path length, the average speed and the orientation angle were measured. After the water maze test was finished, the step-down test was performed, and the number of electric shocks (or called as the error number) received by each rat within 5 minutes was recorded as the learning performance. The test was performed again after 24 hours, namely, the memory retention test, and the latent period for stepping-down the platform for the first time and the error number in five minutes were recorded. After the step-down test was finished, the brain was taken quickly for pathological examination, and the pathological changes of the hippocampus and the cortex were observed.

(3) Test Results

Figure 19:
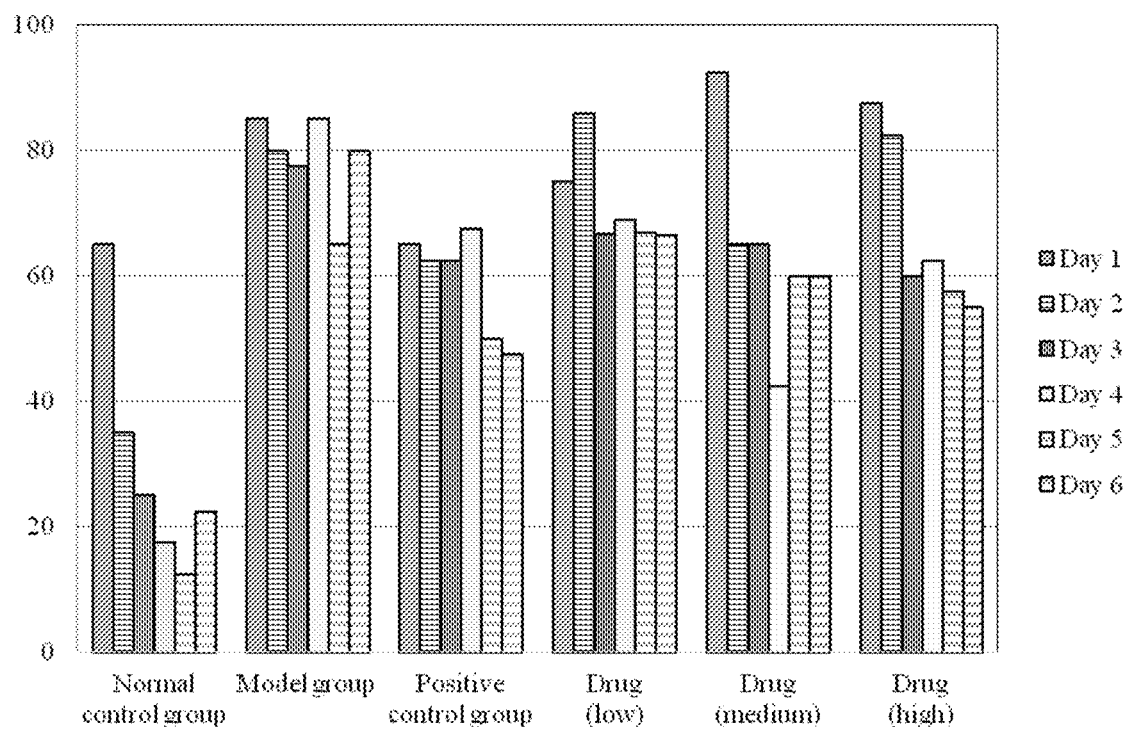
FIG. 19 shows the effect of Crystal Form A on the strategy for reaching the platform of the common carotid artery occlusion-induced vascular dementia rats (peripheral and random)

Compared with the normal control group, for the rats in the model group, on Day 2 to Day 6, the latent period for reaching the platform and the swimming path length were obviously prolonged (P<0.05 or P<0.01), on Day 6, the orientation angle was obviously increased (P<0.05), on Day 1 to Day 6, the swimming speed was not obviously changed, on Day 7, the number of rats crossing the platform within 2 minutes, the residence time in the platform area, the residence time in the platform quadrants and the percentage of the swimming path length in the platform area quadrants to the total swimming path length were all obviously reduced (P<0.05 or P<0.01), the average speed and the orientation angle were not obviously changed, the conversion from the peripheral type or the random type to the tendency type or the linear type in the strategy for looking for the platform was obviously slowed down (P<0.05 or P<0.01), on Day 1 and Day 2, the step-down error number was obviously increased (P<0.05), on Day 2, the error latency was obviously shortened (P<0.05); compared with the model group, for the rats in the dose group of 1.4 mg/kg Crystal Form A of octahydroaminoacridine succinate in the water maze, on Day 4 to Day 6, the latent period for reaching the platform was obviously shortened (P<0.05 or P<0.01), on Day 4, the swimming path length for reaching the platform was obviously shortened (P<0.05), for the rats in the dose group of 2.8 mg/kg Crystal Form A of octahydroaminoacridine succinate in the water maze, on Day 3 to Day 6, the latent period for reaching the platform was obviously shortened (P<0.05 or P<0.01), on Day 3, the swimming path length for reaching the platform was obviously shortened (P<0.05), for the dose groups of 0.7, 1.4 and 2.8 mg/kg Crystal Form A of octahydroaminoacridine succinate, on Day 1 to Day 6, the orientation angle and the swimming speed were not obviously changed, for the dose groups of 1.4, and 2.8 mg/kg Crystal Form A of octahydroaminoacridine succinate, on Day 7, the number of rats crossing the platform within 2 minutes was obviously increased (P<0.05), for the dose groups of 0.7, 1.4 and 2.8 mg/kg Crystal Form A of octahydroaminoacridine succinate, the residence time in the platform quadrants, the average speed, the orientation angle and the percentage of the swimming path length in the platform area quadrants to the total swimming path length were not obviously changed, for the dose groups of 1.4, and 2.8 mg/kg Crystal Form A of octahydroaminoacridine succinate, the conversion from the peripheral type or the random type to the tendency type or the linear type in the strategy for looking for the platform was obviously increased (P<0.05 or P<0.01), for the dose group of 2.8 mg/kg Crystal Form A of octahydroaminoacridine succinate, on Day 1 and Day 2 the step-down error number was obviously reduced (P<0.05), on Day 2, the error latency was obviously prolonged (P<0.05), for the dose group of 1.4 mg/kg Crystal Form A of octahydroaminoacridine succinate, on Day 2, the step-down error number was obviously reduced (P<0.05), for the rats in the positive control Group in the water maze, on Day 5 and Day 6, the latent period for reaching the platform was obviously shortened (P<0.05 or P<0.01), on Day 2, Day 3 and Day 6, the swimming path length for reaching the platform was obviously shortened (P<0.05), on Day 1 to Day 6, the orientation angle and the swimming speed were not obviously changed, on Day 7, the residence time of rats in the platform quadrants within 2 minutes was obviously increased (P<0.05), there was an increased trend in the number of crossing the platform, the residence time in the platform area, and the percentage of the swimming path length in the platform area quadrants to the total swimming path length, but no statistical significance, the average speed, and the orientation angle were not obviously changed, the conversion from the peripheral type or the random type to the tendency type or the linear type in the strategy for looking for the platform was obviously increased (P<0.05 or P<0.01), on Day 1 and Day 2, the step-down error number was obviously reduced (P<0.05), on Day 2, the error latency was obviously prolonged (P<0.05). Pathological findings: the dose group of 2.8 mg/kg Crystal Form A of octahydroaminoacridine succinate: no obvious reduction in the number of cortical nerve cells, compared with the model group, nuclear pyknosis, deeply stained necrotic nerve cells, and neurotropic cellular phenomenon were reduced, and no occurrence of encephalomalacia focus and glial nodules. No obvious reduction in the number of hippocampal nerve cells, compared with the model group, the less degenerated and necrotic cells, and occurrence of the neurotropic cellular phenomenon was observed. The pathology of the dose group of 0.7 mg/kg Crystal Form A of octahydroaminoacridine succinate was similar to that of the model group, and the pathologies for the cortical and hippocampal nerve cells of the dose groups of 1.4 mg/kg and 2.8 mg/kg Crystal Form A of octahydroaminoacridine succinate were substantially identical. The dose groups of 1.4 mg/kg and 2.8 mg/kg Crystal Form A of octahydroaminoacridine succinate could relieve the pathological change of the common carotid artery occlusion-induced vascular dementia, and the results are shown in Table 20-26 and FIG. 19.

TABLE 20

Influence of Crystal Form A and Crystal Form K on the time (s) for the rats with common carotid artery occlusion-induced vascular dementia reaching the platform (x ± s)

| Groups | n | Day 1 | Day 2 | Day 3 |
|---|---|---|---|---|
| Normal control group | 10 | 53.78 ± 33.11 | 17.64 ± 13.05* | 9.73 ± 3.95** |
| Model group | 10 | 74.98 ± 30.22 | 57.77 ± 40.89 | 46.91 ± 29.75 |
| Positive control group | 10 | 58.42 ± 23.42 | 33.96 ± 17.06 | 30.17 ± 14.50 |
| Crystal Form A | | | | |
| 0.7 mg/kg | 9 | 60.40 ± 30.23 | 55.04 ± 31.39 | 29.31 ± 15.94 |
| 1.4 mg/kg | 10 | 75.55 ± 32.44 | 38.71 ± 18.28 | 30.21 ± 14.13 |
| 2.8 mg/kg | 10 | 69.25 ± 15.97 | 40.76 ± 23.88 | 21.75 ± 9.58* |
| Crystal Form K | | | | |
| 0.7 mg/kg | 10 | 75.36 ± 14.23 | 57.33 ± 17.88 | 45.78 ± 10.33 |
| 1.4 mg/kg | 10 | 73.45 ± 14.49 | 50.21 ± 20.11 | 44.29 ± 20.13 |
| 2.8 mg/kg | 10 | 70.25 ± 9.82 | 47.36 ± 14.52 | 40.67 ± 13.41 |
| Groups | n | Day 4 | Day 5 | Day 6 |
| Normal control group | 10 | 8.98 ± 5.40** | 7.75 ± 4.72** | 8.53 ± 4.83** |
| Model group | 10 | 43.43 ± 28.99 | 39.02 ± 19.01 | 43.79 ± 22.34 |
| Positive control group | 10 | 23.92 ± 12.45 | 21.94 ± 11.16* | 17.87 ± 12.66** |
| Crystal Form A | | | | |
| 0.7 mg/kg | 9 | 35.34 ± 35.48 | 71.16 ± 34.92 | 37.72 ± 30.12 |
| 1.4 mg/kg | 10 | 19.79 ± 10.95* | 16.28 ± 11.42** | 16.62 ± 8.69** |
| 2.8 mg/kg | 10 | 22.79 ± 10.04* | 21.57 ± 17.15* | 18.98 ± 13.68** |
| Crystal Form K | | | | |
| 0.7 mg/kg | 10 | 40.55 ± 16.73 | 31.42 ± 17.35 | 32.45 ± 21.25 |
| 1.4 mg/kg | 10 | 39.57 ± 18.69 | 34.62 ± 12.48 | 28.21 ± 15.63 |
| 2.8 mg/kg | 10 | 37.88 ± 17.67 | 28.41 ± 8.73 | 29.10 ± 17.83 |

Compared with the model group:

*P < 0.05,

**P < 0.01

TABLE 21

Influence of Crystal Form A and Crystal Form K on the swimming path length (cm) for the rats with common carotid artery occlusion-induced vascular dementia reaching the platform (x ± s)

| Groups | n | Day 1 | Day 2 | Day 3 |
|---|---|---|---|---|
| Normal control group | 10 | 1227.45 ± 760.12 | 509.31 ± 135.55* | 230.08 ± 102.77** |
| Model group | 10 | 1738.58 ± 801.77 | 1258.37 ± 721.46 | 1018.95 ± 546.26 |
| Positive control group | 10 | 1105.00 ± 578.29 | 579.08 ± 316.12* | 606.25 ± 279.18* |
| Crystal Form A | | | | |
| 0.7 mg/kg | 9 | 1250.31 ± 599.61 | 1368.59 ± 636.46 | 698.11 ± 448.85 |
| 1.4 mg/kg | 10 | 1491.17 ± 529.46 | 917.85 ± 346.36 | 804.05 ± 351.90 |
| 2.8 mg/kg | 10 | 1555.98 ± 522.10 | 1025.55 ± 559.44 | 512.17 ± 265.98* |
| Crystal Form K | | | | |
| 0.7 mg/kg | 10 | 1602.41 ± 583.25 | 1242.31 ± 438.47 | 749.48 ± 427.45 |
| 1.4 mg/kg | 10 | 1502.83 ± 613.11 | 1219.38 ± 892.43 | 763.45 ± 414.55 |
| 2.8 mg/kg | 10 | 1211.27 ± 259.82 | 1377.38 ± 328.92 | 644.62 ± 582.37 |

| Groups | n | Day 4 | Day 5 | Day 6 |
|---|---|---|---|---|
| Normal control group | 10 | 236.25 ± 131.98** | 240.17 ± 191.00** | 173.06 ± 63.92** |
| Model group | 10 | 995.57 ± 607.00 | 808.22 ± 421.39 | 754.50 ± 424.09 |
| Positive control group | 10 | 615.78 ± 385.17 | 586.80 ± 405.09 | 348.06 ± 202.65* |
| Crystal Form A | | | | |
| 0.7 mg/kg | 9 | 838.00 ± 799.29 | 878.23 ± 464.48 | 606.62 ± 360.87 |
| 1.4 mg/kg | 10 | 461.53 ± 216.01* | 515.67 ± 565.72 | 393.13 ± 236.85 |
| 2.8 mg/kg | 10 | 827.58 ± 463.98 | 676.75 ± 429.93 | 433.81 ± 327.88 |
| Crystal Form K | | | | |
| 0.7 mg/kg | 10 | 788.25 ± 300.86 | 664.56 ± 562.88 | 523.46 ± 237.12 |
| 1.4 mg/kg | 10 | 752.34 ± 467.22 | 689.43 ± 267.98 | 531.55 ± 169.37 |
| 2.8 mg/kg | 10 | 703.47 ± 231.68 | 642.45 ± 386.45 | 502.78 ± 482.65 |

Compared with the model group:
*$P < 0.05$,
**$P < 0.01$

TABLE 22

Influence of Crystal Form A and Crystal Form K on the orientation angle (°) for the rats with common carotid artery occlusion-induced vascular dementia reaching the platform (x ± s)

| Groups | n | Day 1 | Day 2 | Day 3 |
|---|---|---|---|---|
| Normal control group | 10 | 53.85 ± 18.85 | 55.92 ± 20.91 | 41.48 ± 21.53 |
| Model group | 10 | 61.39 ± 18.49 | 60.28 ± 20.25 | 54.17 ± 16.57 |
| Positive control group | 10 | 58.85 ± 15.35 | 61.54 ± 17.41 | 48.94 ± 13.42 |
| Crystal Form A | | | | |
| 0.7 mg/kg | 9 | 64.44 ± 24.84 | 52.13 ± 14.28 | 57.18 ± 14.54 |
| 1.4 mg/kg | 10 | 63.00 ± 21.34 | 48.91 ± 15.52 | 53.59 ± 14.56 |
| 2.8 mg/kg | 10 | 75.34 ± 20.00 | 57.20 ± 22.99 | 41.65 ± 17.28 |
| Crystal Form K | | | | |
| 0.7 mg/kg | 10 | 68.46 ± 25.21 | 60.47 ± 24.23 | 59.03 ± 16.89 |
| 1.4 mg/kg | 10 | 69.28 ± 21.03 | 58.29 ± 17.83 | 58.22 ± 10.34 |
| 2.8 mg/kg | 10 | 70.38 ± 18.48 | 57.88 ± 17.43 | 55.11 ± 16.99 |

| Groups | n | Day 4 | Day 5 | Day 6 |
|---|---|---|---|---|
| Normal control group | 10 | 37.48 ± 16.13 | 34.77 ± 18.58 | 35.39 ± 19.16* |
| Model group | 10 | 54.27 ± 22.61 | 46.98 ± 11.38 | 53.34 ± 15.85 |
| Positive control group | 10 | 58.94 ± 22.56 | 49.64 ± 17.65 | 53.54 ± 19.68 |
| Crystal Form A | | | | |
| 0.7 mg/kg | 9 | 55.89 ± 20.65 | 62.38 ± 27.61 | 46.48 ± 22.04 |
| 1.4 mg/kg | 10 | 50.23 ± 20.86 | 55.03 ± 19.71 | 53.94 ± 12.47 |
| 2.8 mg/kg | 10 | 57.00 ± 17.94 | 55.78 ± 27.48 | 52.70 ± 15.27 |
| Crystal Form K | | | | |
| 0.7 mg/kg | 10 | 55.36 ± 19.61 | 53.56 ± 14.56 | 50.39 ± 22.30 |
| 1.4 mg/kg | 10 | 53.49 ± 14.67 | 52.76 ± 19.40 | 50.34 ± 20.04 |
| 2.8 mg/kg | 10 | 50.35 ± 15.5 | 53.49 ± 23.42 | 46.37 ± 26.8 |

Compared with the model group:
*$P < 0.05$

TABLE 23

Influence of Crystal Form A and Crystal Form K on the speed (cm/s) for the rats with common carotid artery occlusion-induced vascular dementia reaching the platform (x ± s)

| Groups | n | Day 1 | Day 2 | Day 3 |
|---|---|---|---|---|
| Normal control group | 10 | 26.18 ± 8.95 | 29.39 ± 7.35 | 22.75 ± 4.01 |
| Model group | 10 | 21.49 ± 5.57 | 23.70 ± 7.83 | 22.29 ± 3.93 |
| Positive control group | 10 | 21.15 ± 5.56 | 22.68 ± 5.82 | 21.19 ± 3.15 |
| Crystal Form A | | | | |
| 0.7 mg/kg | 9 | 21.68 ± 6.14 | 23.68 ± 5.10 | 26.27 ± 6.15 |
| 1.4 mg/kg | 10 | 22.93 ± 7.28 | 29.02 ± 6.70 | 25.25 ± 5.42 |
| 2.8 mg/kg | 10 | 23.52 ± 5.71 | 28.32 ± 7.08 | 24.59 ± 6.25 |
| Crystal Form K | | | | |
| 0.7 mg/kg | 10 | 21.26 ± 4.78 | 21.66 ± 8.76 | 20.12 ± 8.22 |
| 1.4 mg/kg | 10 | 20.45 ± 9.24 | 24.28 ± 9.65 | 21.34 ± 6.99 |
| 2.8 mg/kg | 10 | 19.88 ± 6.76 | 28.24 ± 4.72 | 20.10 ± 6.82 |

TABLE 23-continued

Influence of Crystal Form A and Crystal Form K on the speed (cm/s) for the rats with common carotid artery occlusion-induced vascular dementia reaching the platform (x ± s)

| Groups | n | Day 4 | Day 5 | Day 6 |
|---|---|---|---|---|
| Normal control group | 10 | 30.54 ± 7.46 | 29.00 ± 5.46 | 24.23 ± 5.78 |
| Model group | 10 | 25.85 ± 8.09 | 24.55 ± 6.46 | 20.78 ± 5.39 |
| Positive control group | 10 | 25.79 ± 9.79 | 24.88 ± 8.76 | 21.02 ± 6.67 |
| Crystal Form A | | | | |
| 0.7 mg/kg | 9 | 25.53 ± 8.12 | 24.14 ± 7.38 | 22.02 ± 6.73 |
| 1.4 mg/kg | 10 | 28.54 ± 9.09 | 29.15 ± 10.97 | 23.52 ± 2.43 |
| 2.8 mg/kg | 10 | 27.72 ± 6.59 | 27.44 ± 4.86 | 23.55 ± 2.66 |
| Crystal Form K | | | | |
| 0.7 mg/kg | 10 | 21.70 ± 10.21 | 21.42 ± 7.22 | 19.52 ± 14.27 |
| 1.4 mg/kg | 10 | 20.28 ± 6.02 | 21.26 ± 8.46 | 22.54 ± 9.36 |
| 2.8 mg/kg | 10 | 21.00 ± 5.91 | 22.93 ± 6.31 | 21.32 ± 7.46 |

TABLE 24

Influence of Crystal Form A and Crystal Form K on the adopted strategy for the rats with common carotid artery occlusion-induced dementia reaching the platform (the peripheral type and the random type %)

| Groups | n | Day 1 | Day 2 | Day 3 | Day 4 | Day 5 | Day 6 |
|---|---|---|---|---|---|---|---|
| Normal control group | 10 | 65.00* | 35.00** | 25.00** | 17.50** | 12.50** | 22.50** |
| Model group | 10 | 85.00 | 80.00 | 77.50 | 85.00 | 65.00 | 80.00 |
| Positive control group Crystal Form A | 10 | 65.00* | 62.50 | 62.50* | 67.50 | 50.00 | 47.50** |
| 0.7 mg/kg | 9 | 75.00 | 86.00 | 66.67 | 69.00 | 67.00 | 66.60 |
| 1.4 mg/kg | 10 | 92.50 | 65.00 | 65.00* | 42.50** | 60.00 | 60.00* |
| 2.8 mg/kg | 10 | 87.50 | 82.50 | 60.00* | 62.50* | 57.50 | 55.00* |
| Crystal Form K | | | | | | | |
| 0.7 mg/kg | 10 | 93.00 | 83.50 | 70.50 | 75.50 | 72.50 | 70.00 |
| 1.4 mg/kg | 10 | 86.50 | 80.00 | 71.00 | 68.00 | 62.00 | 66.50 |
| 2.8 mg/kg | 10 | 79.00 | 76.50 | 65.50 | 62.50 | 58.50 | 54.00 |

Compared with the model group: *P < 0.05, **P < 0.01

TABLE 25

Influence of Crystal Form A and Crystal Form K on the rats with the common carotid artery occlusion-induced vascular dementia in water maze on Day 7

| Groups | n | Time in the platform area (s) | Number of crossing the platform | Time in the platform quadrants (s) |
|---|---|---|---|---|
| Normal control group | 10 | 4.23 ± 2.03* | 13.60 ± 5.48** | 45.32 ± 9.36** |
| Model group | 10 | 2.27 ± 1.18 | 6.60 ± 3.41 | 33.19 ± 4.33 |
| Positive control group Crystal Form A | 10 | 3.06 ± 2.24 | 9.40 ± 5.16 | 42.21 ± 12.71* |
| 0.7 mg/kg | 9 | 1.86 ± 1.78 | 5.55 ± 4.47 | 33.93 ± 11.68 |
| 1.4 mg/kg | 10 | 3.18 ± 2.02 | 12.20 ± 5.99* | 40.31 ± 12.72 |
| 2.8 mg/kg | 10 | 3.23 ± 3.70 | 10.40 ± 4.40* | 33.72 ± 10.48 |
| Crystal Form K | | | | |
| 0.7 mg/kg | 10 | 2.87 ± 2.14 | 5.67 ± 3.45 | 35.61 ± 10.91 |
| 1.4 mg/kg | 10 | 2.18 ± 2.34 | 7.25 ± 2.45 | 37.88 ± 12.37 |
| 2.8 mg/kg | 10 | 2.56 ± 3.27 | 7.49 ± 3.51 | 34.52 ± 15.82 |

| Groups | Swimming path length in the platform area/total swimming path length × 100% | Average speed (cm/s) | Orientation angle (°) |
|---|---|---|---|
| Normal control group | 35.97 ± 6.36** | 26.46 ± 4.91 | 11.60 ± 5.48 |
| Model group | 27.95 ± 3.56 | 23.69 ± 6.52 | 6.60 ± 3.41 |
| Positive control group Crystal Form A | 33.02 ± 9.98 | 24.60 ± 10.18 | 9.40 ± 5.17 |
| 0.7 mg/kg | 26.83 ± 7.77 | 24.04 ± 7.96 | 5.56 ± 4.47 |
| 1.4 mg/kg | 31.89 ± 9.92 | 28.44 ± 9.02 | 12.20 ± 5.99 |
| 2.8 mg/kg | 28.40 ± 8.75 | 26.15 ± 5.40 | 10.40 ± 4.40 |
| Crystal Form K | | | |
| 0.7 mg/kg | 26.88 ± 7.36 | 23.62 ± 8.38 | 27.88 ± 6.57 |
| 1.4 mg/kg | 28.74 ± 8.90 | 24.69 ± 5.76 | 24.69 ± 8.21 |
| 2.8 mg/kg | 27.39 ± 10.42 | 25.45 ± 6.98 | 23.57 ± 4.76 |

Compared with the model group:
*P < 0.05,
**P < 0.01

TABLE 26

Prophylaxis and treatment effect of Crystal Form A and
Crystal Form K on common carotid artery occlusion-induced
vascular dementia in rats (step-down method, n = 10, x ± s)

| Groups | Day 1, Error number | Day 2, Error latency (seconds) | Day 2, Error number |
|---|---|---|---|
| Normal control group | 4.90 ± 3.87* | 246.80 ± 63.59* | 0.90 ± 1.10* |
| Model group | 9.10 ± 3.90 | 159.80 ± 88.15 | 3.80 ± 3.04 |
| Positive control group | 5.40 ± 3.06* | 244.10 ± 77.83* | 1.10 ± 1.28* |
| Crystal Form A | | | |
| 0.7 mg/kg | 7.50 ± 4.06 | 215.30 ± 83.07 | 1.70 ± 1.49 |
| 1.4 mg/kg | 6.60 ± 2.88 | 223.70 ± 75.02 | 1.30 ± 1.25* |
| 2.8 mg/kg | 5.80 ± 2.65* | 250.10 ± 72.32* | 0.90 ± 1.28* |
| Crystal Form K | | | |
| 0.7 mg/kg | 9.21 ± 4.52 | 146.89 ± 60.45 | 2.49 ± 2.35 |
| 1.4 mg/kg | 8.34 ± 3.78 | 178.46 ± 52.77 | 3.34 ± 1.49 |
| 2.8 mg/kg | 8.46 ± 4.68 | 192.55 ± 87.48 | 3.41 ± 1.88 |

Compared with the model group:
*P < 0.05,
**P < 0.05

It can be seen from the effects of the above animal experiments that Crystal Form A shows better in vivo treatment effect compared with the comparative example Crystal Form K in the prior art.

Finally, it should be noted that: the above examples are only intended to illustrate the technical solution of the present invention, but not to limit it; although the present invention has been described in detail with reference to the foregoing embodiments, it should be understood by those of ordinary skill in the art that: the technical solutions described in the foregoing embodiments may still be modified, or some technical features may be equivalently replaced; and such modifications or substitutions do not depart from the spirit and scope of the corresponding technical solutions of the embodiments of the present invention.

What is claimed is:

1. A crystal form of octahydroaminoacridine succinate, wherein said crystal form is any one of the following crystal forms:
    Crystal Form A, characterized by main characteristic X-ray powder diffraction peaks at the corresponding positions of 2θ values of 8.8°±0.2°, 16.4°±0.2°, 23.2°±0.2°;
    Crystal Form C, characterized by main characteristic X-ray powder diffraction peaks at the corresponding positions of 2θ values of 8.0°±0.2°, 24.1°±0.2°, 21.7°±0.2°;
    Crystal Form F, characterized by main characteristic X-ray powder diffraction peaks at the corresponding positions of 2θ values of 21.3°±0.2°, 7.1°±0.2°, 26.3°±0.2°.

2. The crystal form of octahydroaminoacridine succinate of claim 1, wherein
    said Crystal Form A is further characterized by secondary characteristic X-ray powder diffraction peaks at the corresponding positions of 2θ values of 17.0°±0.2°, 17.8°±0.2°, 23.8°±0.2°;
    said Crystal Form C is further characterized by secondary characteristic X-ray powder diffraction peaks at the corresponding positions of 2θ values of 25.5°±0.2°, 22.8°±0.2°, 17.0°±0.2°;
    said Crystal Form F is further characterized by secondary characteristic X-ray powder diffraction peaks at the corresponding positions of 2θ values of 24.2°±0.2°, 8.3°±0.2°, 14.2°±0.2°.

3. The crystal form of octahydroaminoacridine succinate of claim 2, wherein said crystal form is Crystal Form A, and said Crystal Form A is further characterized by tertiary characteristic X-ray powder diffraction peaks at the corresponding positions of 2θ values of 12.1°±0.2°, 8.2°±0.2°, 9.3°±0.2°.

4. The crystal form of octahydroaminoacridine succinate of claim 1, wherein:
    said Crystal Form A has an X-ray powder diffraction pattern substantially as shown in FIG. 1;
    said Crystal Form C has an X-ray powder diffraction pattern substantially as shown in FIG. 2; and
    said Crystal Form F has an X-ray powder diffraction pattern substantially as shown in FIG. 3.

5. A process for preparing a crystal form of octahydroaminoacridine succinate, comprising:
    preparing a Crystal Form A of octahydroaminoacridine succinate by any one of: an anti-solvent addition test, an anti-anti-solvent addition test, gas-solid diffusion, slow volatilization, slow cooling, suspension stirring at room temperature, suspension stirring at 50° C., suspension stirring at 70° C., cyclical stirring at 50-5° C., gas-liquid diffusion, high polymer induced crystallization with volatilization, or high polymer induced crystallization with stirring and grinding, wherein said Crystal Form A is characterized by main characteristic X-ray powder diffraction peaks at the corresponding positions of 2θ values of 8.8°±0.2°, 16.4°±0.2°, 23.2°±0.2°;
    preparing a Crystal Form C of octahydroaminoacridine succinate by any one of: an anti-solvent addition test, an anti-anti-solvent addition test, slow cooling, suspension stirring at room temperature, suspension stirring at 50° C., suspension stirring at 70° C., cyclical stirring at 50-5° C., and gas-liquid diffusion, wherein said Crystal Form C is characterized by main characteristic X-ray powder diffraction peaks at the corresponding positions of 2θ values of 8.0°±0.2°, 24.1°±0.2°, 21.7°±0.2°; or
    preparing a Crystal Form F of octahydroaminoacridine succinate by any one of gas-solid diffusion or suspension stirring at room temperature, wherein said Crystal Form F is characterized by main characteristic X-ray powder diffraction peaks at the corresponding positions of 2θ values of 21.3°±0.2°, 7.1°±0.2°, 26.3°±0.2°.

6. A pharmaceutical composition, comprising an effective amount of one or more of:
    an effective amount of a Crystal Form A of octahydroaminoacridine succinate, wherein said Crystal form A is characterized by main characteristic X-ray powder diffraction peaks at the corresponding positions of 2θ values of 8.8°±0.2°, 16.4°±0.2°, 23.2°±0.2°;
    an effective amount of a Crystal Form C of octahydroaminoacridine succinate, wherein said Crystal Form C is characterized by main characteristic X-ray powder diffraction peaks at the corresponding positions of 2θ values of 8.0°±0.2°, 24.1°±0.2°, 21.7°±0.2°;
    an effective amount of a Crystal Form F of octahydroaminoacridine succinate, wherein said Crystal Form F is characterized by main characteristic X-ray powder diffraction peaks at the corresponding positions of 2θ values of 21.3°±0.2°, 7.1°±0.2°, 26.3°±0.2°.

7. A method of treating a disease caused by excessive activation of cholinesterase or a disease related to decreased choline function, comprising:
  administering an effective amount of a crystal form of octahydroaminoacridine succinate to a patient in need thereof, wherein said crystal form of octahydroaminoacridine succinate is one or more of:
  Crystal Form A of octahydroaminoacridine succinate, wherein said Crystal form A is characterized by main characteristic X-ray powder diffraction peaks at the corresponding positions of 2θ values of 8.8°±0.2°, 16.4°±0.2°, 23.2°±0.2°;
  Crystal Form C of octahydroaminoacridine succinate, wherein said Crystal Form C is characterized by main characteristic X-ray powder diffraction peaks at the corresponding positions of 2θ values of 8.0°±0.2°, 24.1°±0.2°, 21.7°±0.2°;
  Crystal Form F of octahydroaminoacridine succinate, wherein said Crystal Form F is characterized by main characteristic X-ray powder diffraction peaks at the corresponding positions of 2θ values of 21.3°±0.2°, 7.1°±0.2°, 26.3°±0.2°.

8. The method of claim 7, wherein:
  said disease caused by excessive activation of cholinesterase is selected from the group consisting of: Alzheimer disease, myasthenia gravis, myatrophy, poliomyelitis sequelae, childhood cerebral palsy, traumatic sensorimotor disorder, polyneuritis and radiculitis, abdominal distension, urine retention, paroxysmal supraventricular tachycardia, rescue of non-depolarizing muscular relaxant poisoning, glaucoma, muscle relaxant antagonism, inflammation, kidney disease, obesity, fatty liver, hyperthyroidism, schizophrenia, hemolytic anemia, and megaloblastic anemia; and
  said disease related to decreased choline function is selected from the group consisting of: insomnia, vascular dementia, memory loss, attention deficit disorder, and choline depletion-related cognitive impairment disease.

9. The process of claim 5, wherein:
  said Crystal Form A is further characterized by secondary characteristic X-ray powder diffraction peaks at the corresponding positions of 2θ values of 17.0°±0.2°, 17.8°±0.2°, 23.8°±0.2°;
  said Crystal Form C is further characterized by secondary characteristic X-ray powder diffraction peaks at the corresponding positions of 2θ values of 25.5°±0.2°, 22.8°±0.2°, 17.0°±0.2°;
  said Crystal Form F is further characterized by secondary characteristic X-ray powder diffraction peaks at the corresponding positions of 2θ values of 24.2°±0.2°, 8.3°±0.2°, 14.2°±0.2°.

10. The process of claim 9, wherein said process produces said Crystal Form A, and said Crystal Form A is further characterized by tertiary characteristic X-ray powder diffraction peaks at the corresponding positions of 2θ values of 12.1°±0.2°, 8.2°±0.2°, 9.3°±0.2°.

11. The process of claim 5, wherein:
  said Crystal Form A has an X-ray powder diffraction pattern substantially as shown in FIG. 1;
  said Crystal Form C has an X-ray powder diffraction pattern substantially as shown in FIG. 2; and
  said Crystal Form F has an X-ray powder diffraction pattern substantially as shown in FIG. 3.

12. The pharmaceutical composition of claim 6, wherein:
  said Crystal Form A is further characterized by secondary characteristic X-ray powder diffraction peaks at the corresponding positions of 2θ values of 17.0°±0.2°, 17.8°±0.2°, 23.8°±0.2°;
  said Crystal Form C is further characterized by secondary characteristic X-ray powder diffraction peaks at the corresponding positions of 2θ values of 25.5°±0.2°, 22.8°±0.2°, 17.0°±0.2°;
  said Crystal Form F is further characterized by secondary characteristic X-ray powder diffraction peaks at the corresponding positions of 2θ values of 24.2°±0.2°, 8.3°±0.2°, 14.2°±0.2°.

13. The pharmaceutical composition of claim 12, wherein said Crystal Form A is further characterized by tertiary characteristic X-ray powder diffraction peaks at the corresponding positions of 2θ values of 12.1°±0.2°, 8.2°±0.2°, 9.3°±0.2°.

14. The pharmaceutical composition of claim 6, wherein:
  said Crystal Form A has an X-ray powder diffraction pattern substantially as shown in FIG. 1;
  said Crystal Form C has an X-ray powder diffraction pattern substantially as shown in FIG. 2; and
  said Crystal Form F has an X-ray powder diffraction pattern substantially as shown in FIG. 3.

15. The method of claim 7, wherein:
  said Crystal Form A is further characterized by secondary characteristic X-ray powder diffraction peaks at the corresponding positions of 2θ values of 17.0°±0.2°, 17.8°±0.2°, 23.8°±0.2°;
  said Crystal Form C is further characterized by secondary characteristic X-ray powder diffraction peaks at the corresponding positions of 2θ values of 25.5°±0.2°, 22.8°±0.2°, 17.0°±0.2°;
  said Crystal Form F is further characterized by secondary characteristic X-ray powder diffraction peaks at the corresponding positions of 2θ values of 24.2°±0.2°, 8.3°±0.2°, 14.2°±0.2°.

16. The method of claim 15, wherein said Crystal Form A is further characterized by tertiary characteristic X-ray powder diffraction peaks at the corresponding positions of 2θ values of 12.1°±0.2°, 8.2°±0.2°, 9.3°±0.2°.

17. The method of claim 7, wherein:
  said Crystal Form A has an X-ray powder diffraction pattern substantially as shown in FIG. 1;
  said Crystal Form C has an X-ray powder diffraction pattern substantially as shown in FIG. 2; and
  said Crystal Form F has an X-ray powder diffraction pattern substantially as shown in FIG. 3.

18. The method of claim 8, wherein:
  said Crystal Form A is further characterized by secondary characteristic X-ray powder diffraction peaks at the corresponding positions of 2θ values of 17.0°±0.2°, 17.8°±0.2°, 23.8°±0.2°;
  said Crystal Form C is further characterized by secondary characteristic X-ray powder diffraction peaks at the corresponding positions of 2θ values of 25.5°±0.2°, 22.8°±0.2°, 17.0°±0.2°;
  said Crystal Form F is further characterized by secondary characteristic X-ray powder diffraction peaks at the corresponding positions of 2θ values of 24.2°±0.2°, 8.3°±0.2°, 14.2°±0.2°.

19. The method of claim 18, wherein said Crystal Form A is further characterized by tertiary characteristic X-ray powder diffraction peaks at the corresponding positions of 2θ values of 12.1°±0.2°, 8.2°±0.2°, 9.3°±0.2°.

20. The method of claim 8, wherein:

said Crystal Form A has an X-ray powder diffraction pattern substantially as shown in FIG. 1;

said Crystal Form C has an X-ray powder diffraction pattern substantially as shown in FIG. 2; and said Crystal Form F has an X-ray powder diffraction pattern substantially as shown in FIG. 3.

\* \* \* \* \*